United States Patent
Seo

(10) Patent No.: US 10,463,914 B2
(45) Date of Patent: Nov. 5, 2019

(54) ELECTRONIC DEVICE

(71) Applicant: LG ELECTRONICS INC., Seoul (KR)

(72) Inventor: Jeongchul Seo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 36 days.

(21) Appl. No.: 15/021,156

(22) PCT Filed: Jan. 29, 2014

(86) PCT No.: PCT/KR2014/000842
§ 371 (c)(1),
(2) Date: Mar. 10, 2016

(87) PCT Pub. No.: WO2015/037792
PCT Pub. Date: Mar. 19, 2015

(65) Prior Publication Data
US 2016/0220865 A1    Aug. 4, 2016

(30) Foreign Application Priority Data

Sep. 10, 2013 (KR) .................. 10-2013-0108744
Oct. 21, 2013 (KR) .................. 10-2013-0125436

(51) Int. Cl.
*A63B 24/00* (2006.01)
*G06F 1/16* (2006.01)
(Continued)

(52) U.S. Cl.
CPC .......... *A63B 24/0062* (2013.01); *G06F 1/163* (2013.01); *G06F 1/1694* (2013.01);
(Continued)

(58) Field of Classification Search
CPC .......... A63B 2220/836; A63B 24/0062; A63B 2071/0663; A63B 2220/803;
(Continued)

(56) References Cited

U.S. PATENT DOCUMENTS

| 8,251,875 B2 | 8/2012 | Ellis et al. | |
| 2005/0070809 A1* | 3/2005 | Acres | A61B 5/0006 600/508 |

(Continued)

FOREIGN PATENT DOCUMENTS

| CN | 102968267 A | 3/2013 |
| CN | 103212197 A | 7/2013 |

(Continued)

OTHER PUBLICATIONS

Internet disclosure, "Vectorform Working on Apps for Rumored Next Generation Smartwatches," https://www.prweb.com/releases/vectorform/smartwatches/prweb10503867.htm, Royal Oak, MI (PRWEB) Mar. 7, 2013, XP055502879, 4 pages.

*Primary Examiner* — Sanjiv D. Patel
(74) *Attorney, Agent, or Firm* — Birch, Stewart, Kolasch & Birch, LLP

(57) ABSTRACT

The electronic device according to an embodiment of the present disclosure may create exercise data of a user on the basis of data obtained through a sensing unit and provide the created exercise data, and may perform various functions by interworking with a peripheral device.

10 Claims, 28 Drawing Sheets

(51) Int. Cl.
  *G06F 3/01* (2006.01)
  *G06F 3/0488* (2013.01)
  *G06F 19/00* (2018.01)
  *G06F 3/041* (2006.01)
  *G16H 40/63* (2018.01)
  *G16H 15/00* (2018.01)

(52) U.S. Cl.
  CPC .............. *G06F 3/016* (2013.01); *G06F 3/017* (2013.01); *G06F 3/0416* (2013.01); *G06F 3/04883* (2013.01); *G06F 19/3418* (2013.01); *G06F 19/3481* (2013.01); *G16H 40/63* (2018.01); *G06F 2203/04102* (2013.01); *G06F 2203/04104* (2013.01); *G16H 15/00* (2018.01)

(58) Field of Classification Search
  CPC ........................ A63B 2024/0065–0071; A63B 2071/0661–0663; G06F 1/163; G06F 3/015; G06F 3/0346; G06F 3/041–048; A61H 2201/165; A61H 2201/5097; A61H 2201/5046; H04M 1/7253; H04M 2250/02; H04M 2250/12; H04M 1/6066; H04M 3/42042; G06Q 20/1085
  See application file for complete search history.

(56) References Cited

U.S. PATENT DOCUMENTS

| | | | | |
|---|---|---|---|---|
| 2008/0163130 A1* | 7/2008 | Westerman | ......... | G06F 3/04883 715/863 |
| 2009/0059730 A1* | 3/2009 | Lyons | .................... | G04G 21/08 368/69 |
| 2009/0195350 A1* | 8/2009 | Tsern | .................... | G06F 1/1626 340/3.1 |
| 2009/0199130 A1 | 8/2009 | Tsern et al. | | |
| 2009/0270743 A1* | 10/2009 | Dugan | ................. | A61B 5/0002 600/500 |
| 2009/0322699 A1* | 12/2009 | Hansson | ............... | G06F 3/0416 345/174 |
| 2010/0009810 A1* | 1/2010 | Trzecieski | ......... | A63B 24/0062 482/8 |
| 2010/0023895 A1* | 1/2010 | Benko | ..................... | G06F 3/041 715/863 |
| 2010/0062818 A1* | 3/2010 | Haughay, Jr. | ...... | A63B 24/0062 463/7 |
| 2010/0117837 A1* | 5/2010 | Stirling | ................ | A61B 5/1127 340/573.1 |
| 2011/0018731 A1 | 1/2011 | Linsky et al. | | |
| 2011/0149138 A1* | 6/2011 | Watkins | ................ | G06F 3/0485 348/333.02 |
| 2011/0216036 A1* | 9/2011 | Zhang | ..................... | G06F 3/045 345/174 |
| 2012/0116550 A1* | 5/2012 | Hoffman | ............ | A63B 24/0084 700/91 |
| 2013/0100044 A1 | 4/2013 | Zhao et al. | | |
| 2013/0106684 A1 | 5/2013 | Weast et al. | | |
| 2013/0183901 A1* | 7/2013 | Joergensen | ............ | H04M 1/57 455/41.2 |
| 2013/0234929 A1* | 9/2013 | Libin | ........................ | G06F 3/01 345/156 |
| 2013/0236868 A1* | 9/2013 | Erkkila | .............. | A63B 24/0062 434/247 |
| 2014/0257053 A1* | 9/2014 | Yuen | ................... | G06F 19/3418 600/301 |

FOREIGN PATENT DOCUMENTS

| | | |
|---|---|---|
| EP | 2025368 A2 | 2/2009 |
| KR | 10-2012-0056832 A | 6/2012 |
| KR | 10-2012-0085059 A | 7/2012 |
| KR | 10-2013-0084993 A | 7/2013 |
| WO | WO 2012/061438 A2 | 5/2012 |

* cited by examiner

FIG. 12
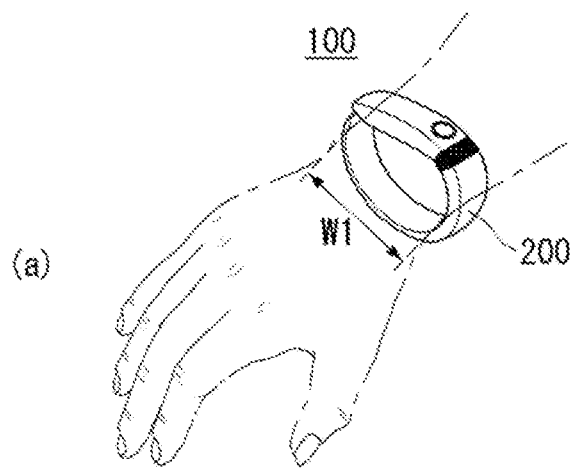
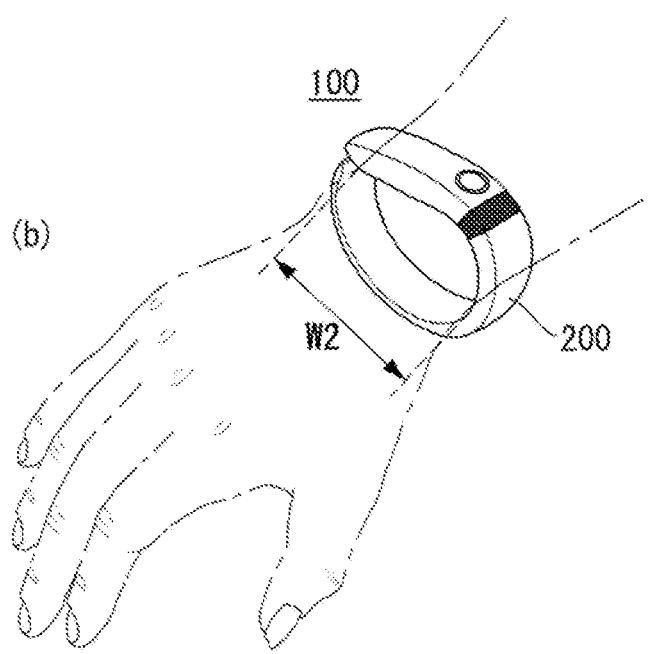

FIG. 13
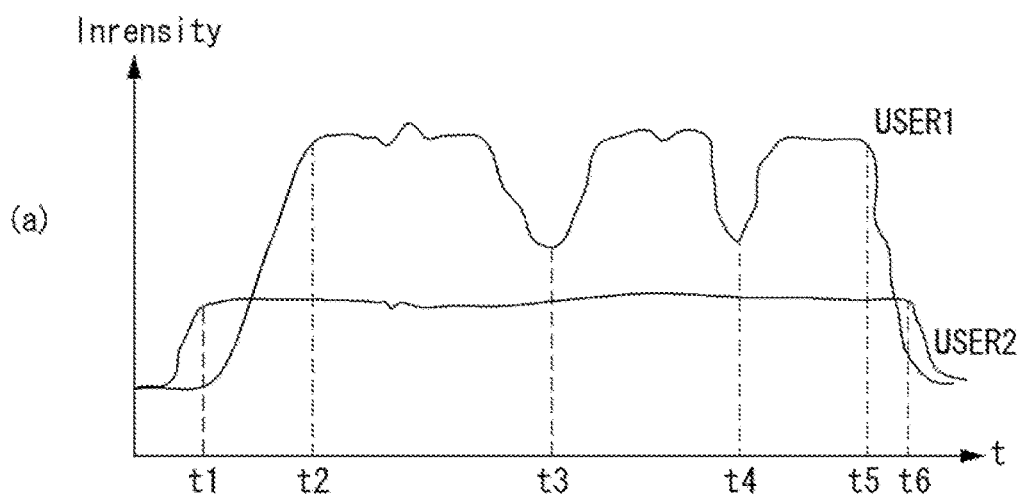
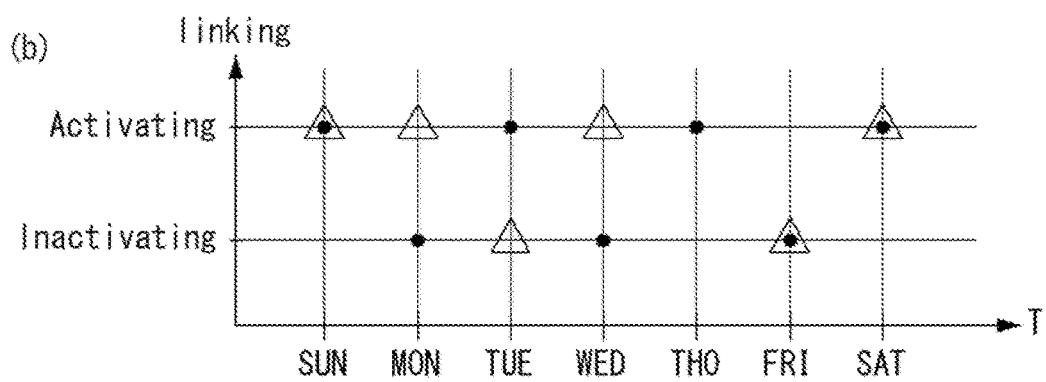

FIG. 17
(a) 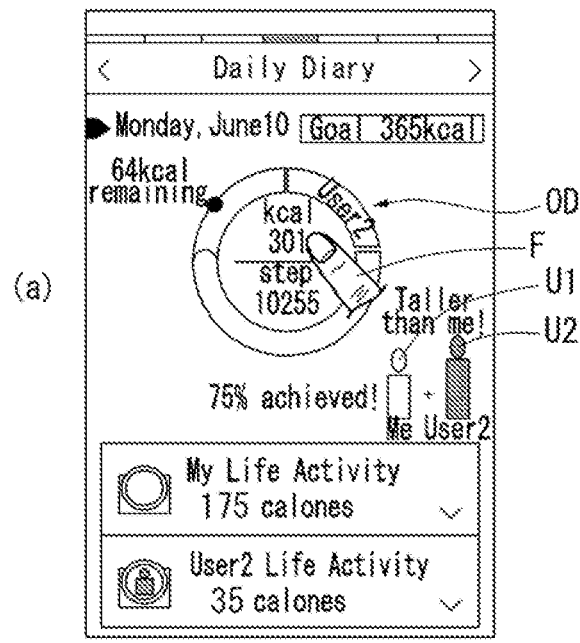
(b) 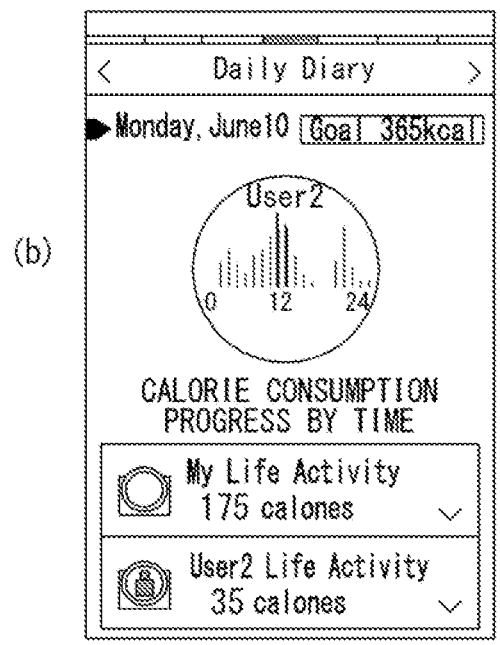

FIG. 18
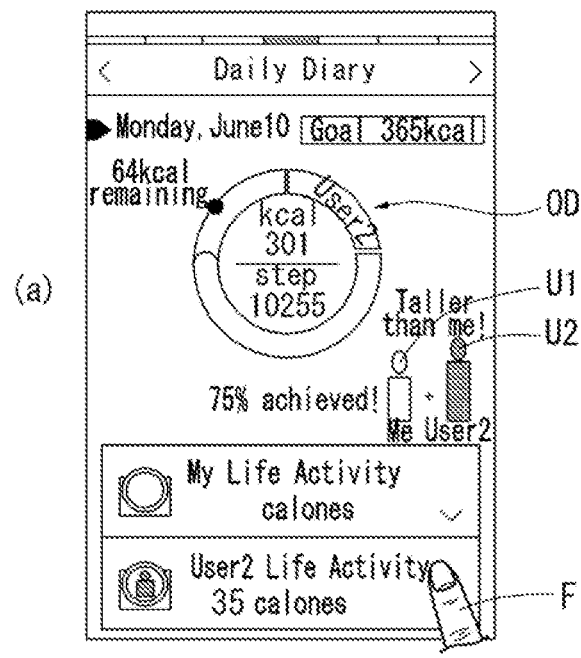
(a)
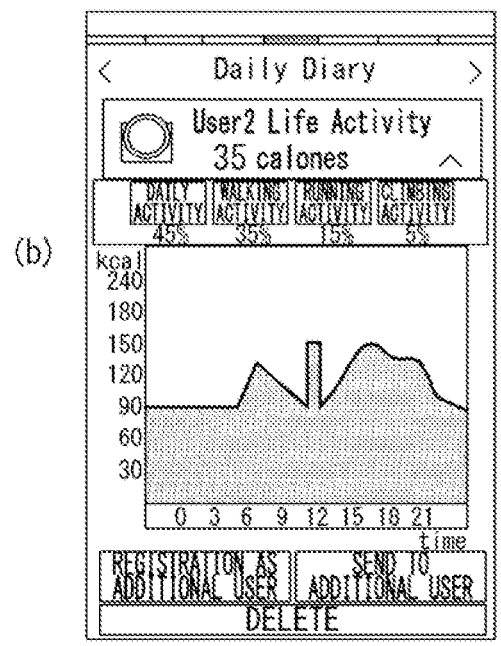
(b)

FIG. 22
(a) 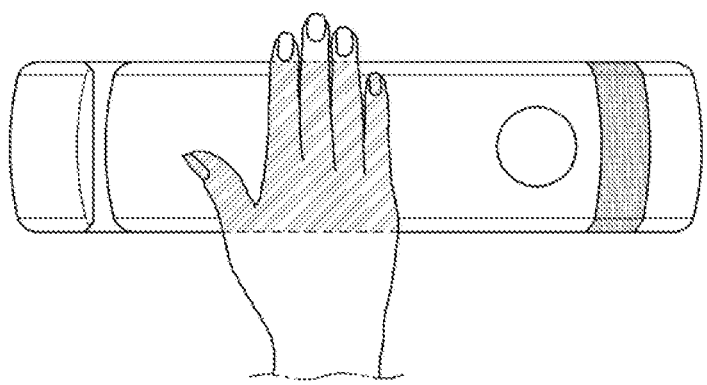
(b) 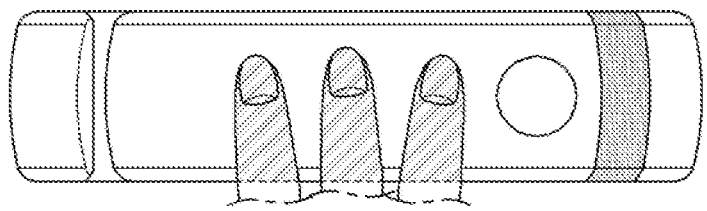
(c) 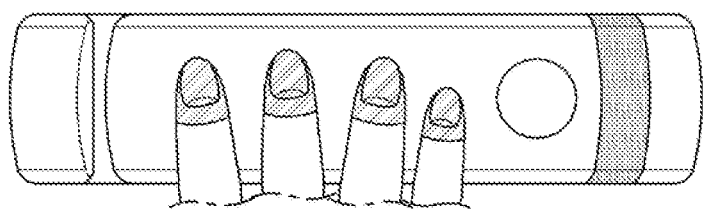
 : touch area

FIG. 24
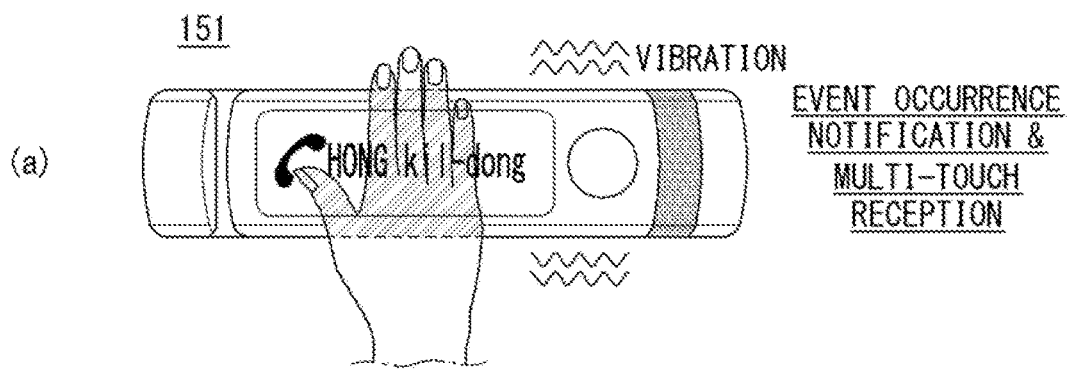
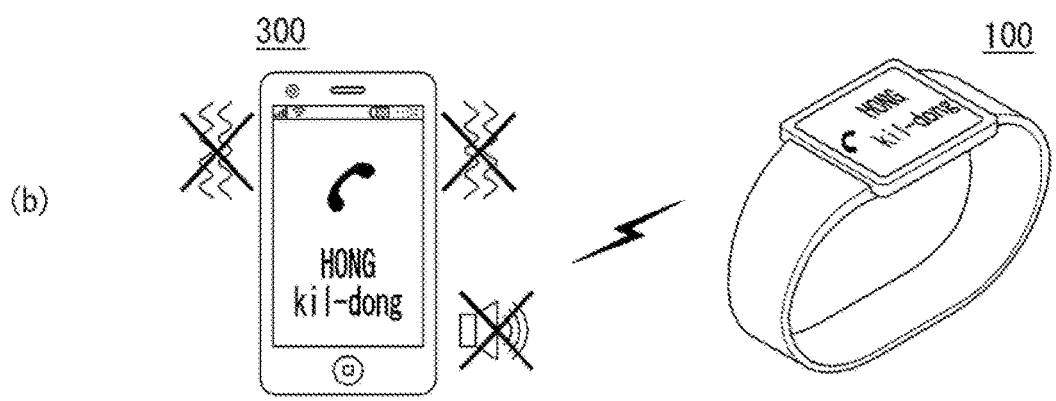
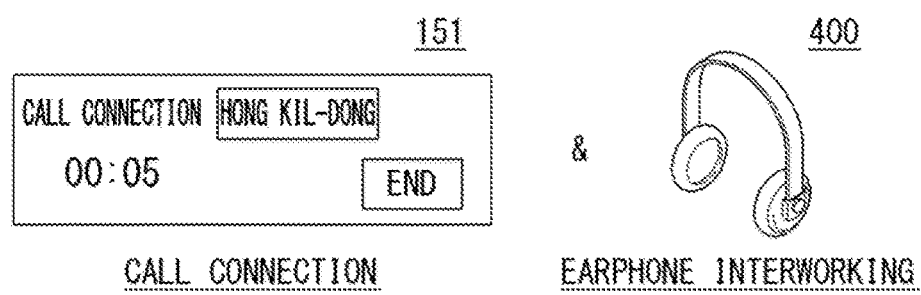

FIG. 25
(a) 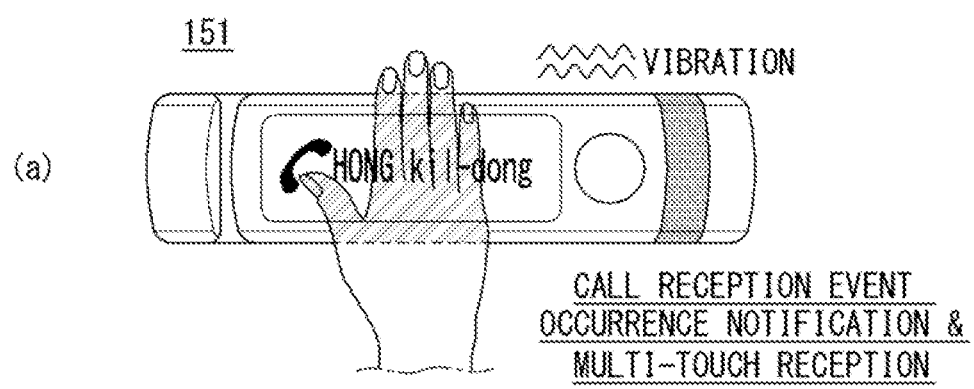
(b) 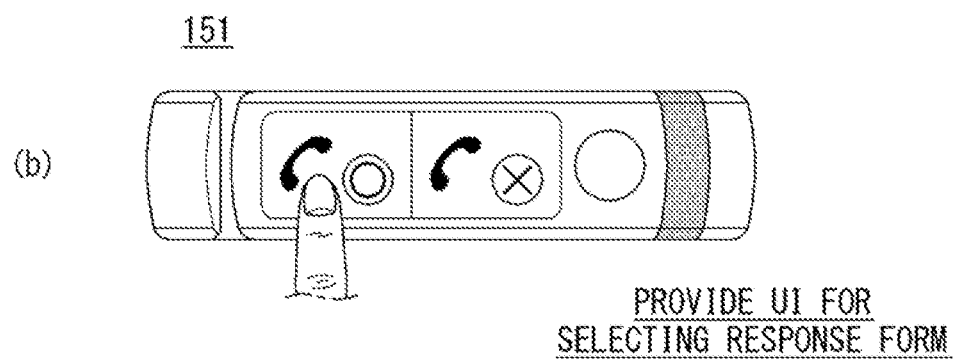

FIG. 26
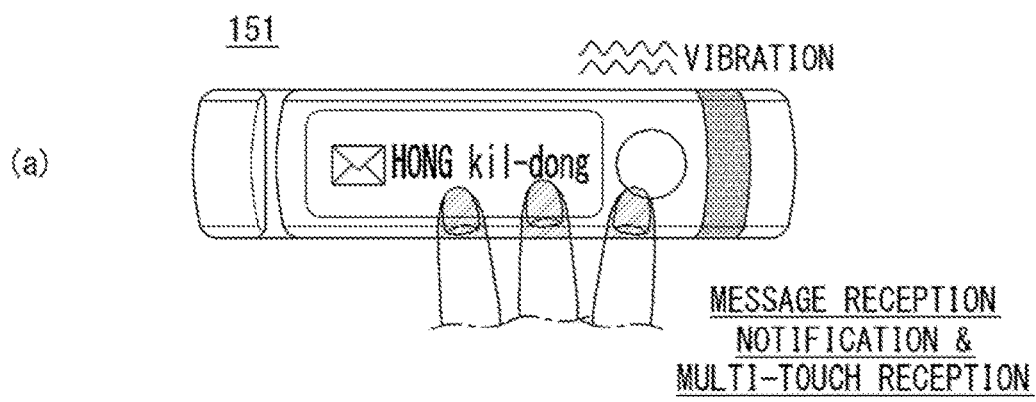
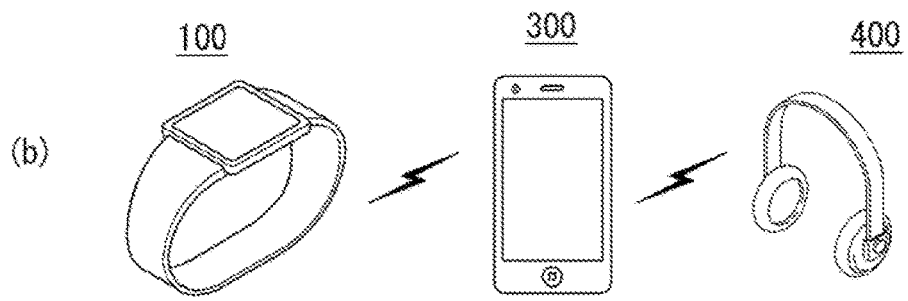

FIG. 30
(a) 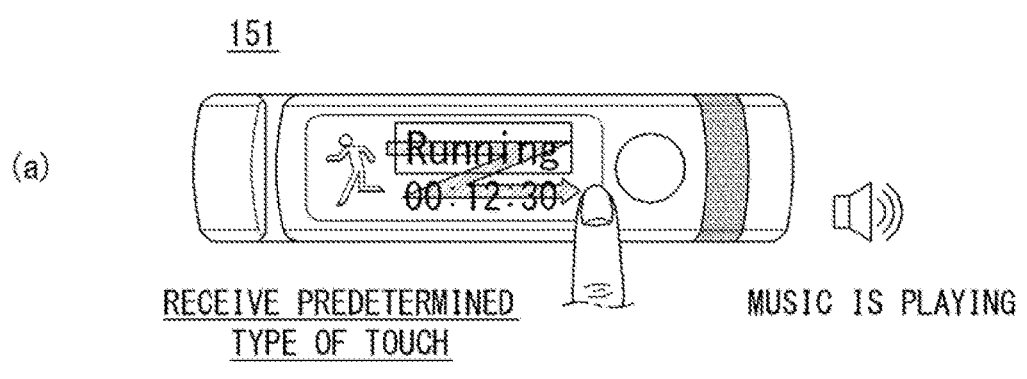
(b) 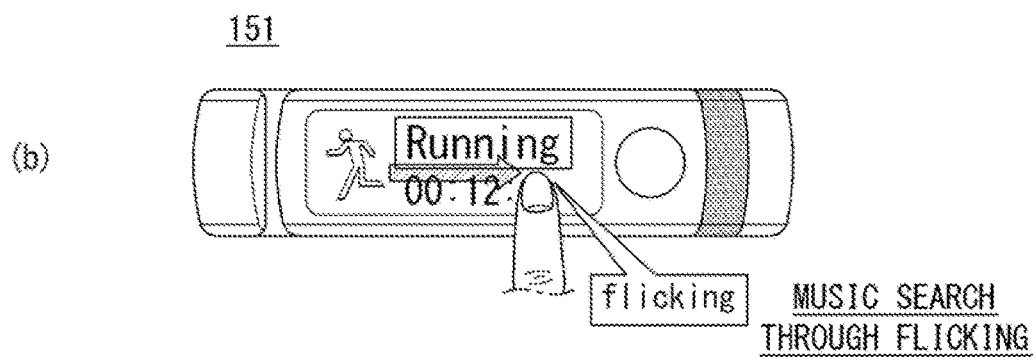

ELECTRONIC DEVICE

CROSS REFERENCE TO RELATED APPLICATIONS

This application is the National Phase of PCT International Application No. PCT/KR2014/000842, filed on Jan. 29, 2014, which claims priority under 35 U.S.C. 119(a) to Patent Application Nos. 10-2013-0108744 and 10-2013-0125436 filed in the Republic of Korea on Sep. 10, 2013 and Oct. 21, 2013, all of which are hereby expressly incorporated by reference into the present application.

TECHNICAL FIELD

The present disclosure relates to an electronic device and, more particularly, to an electronic device capable of generating and providing movement data of a user based on a movement of user's body and performing various functions by interworking with other peripheral device.

BACKGROUND ART

As functions of a terminal such as a personal computer, notebook, mobile phone, and smart phone are diversified, the terminal is now implemented in the form of a multimedia player equipped with multi-functions for capturing pictures or video, playing music or video files, game, and receiving broadcasting programs.

Electronic devices may be classified as mobile/portable terminals and stationary terminals according to whether or not they are portable. Mobile terminals may also be classified as handheld terminals and vehicle-mounted terminals according to whether or not users may be able to directly carry them around.

In order to support and increase the functionality of electronic devices, improvements in structural part and/or software part of terminals may be considered, and in particular, research into and commercialization of wearable electronic devices have been actively conducted.

DISCLOSURE

Technical Problem

Therefore, an object of the present disclosure is to provide an electronic device capable of performing various functions by interworking with another peripheral electronic device, as well as generating movement data of a user by sensing a movement of the user's body

Technical Solution

According to an aspect of the present disclosure, there is provided an electronic device having a band to be worn on a human body. The electronic device may include: a display unit configured to support a touch screen function; a wireless communication unit configured to support a short-range wireless communication function to interwork with a peripheral device; a sensing unit configured to sense movement of a body of a user who wears the electronic device; and a controller.

The controller may create exercise data of the user on the basis of data obtained through the sensing unit, and when a multi-touch is received through the display unit in the exercise mode, the controller may perform predetermined different functions according to an operational state of the electronic device and an operational state of the peripheral device.

When the multi-touch is received and an area of the multi-touch is larger than a predetermined area, regardless of a position in which the touch is received and the number of received touches, the controller may perform a function corresponding to an operational state of the electronic device and an operational state of the peripheral device.

The electronic device may further include a haptic module configured to perform a function of providing information through tactile sensation. Here, the controller may control the display unit and the haptic module to perform a notification function regarding an event which has occurred in the peripheral device, and when the multi-touch is received while the notification function regarding the generated event is being performed, the controller may control the peripheral device to perform a predetermined response function regarding the generated event.

The controller may control the haptic module to generate vibrations having different patterns according to the event which has occurred in the peripheral device.

When a call reception event occurs in the peripheral device and the multi-touch is received while a notification function regarding the call reception event is being performed, the controller may control the peripheral device to interrupt a call reception notification function using a sound or vibration in the peripheral device.

When the multi-touch is received while the notification function regarding the call reception event is being performed, the controller may provide a user interface for determining a response form corresponding to the call reception event through the display unit.

When a message reception event occurs in the peripheral device and the multi-touch is received while a notification function regarding the message reception event is being performed, the controller may control the peripheral device to convert a received message into a voice and output the converted voice.

The controller may vary a data obtaining period through the sensing unit according to an operation mode of the electronic device.

The controller may determine an operation mode of the electronic device on the basis of data obtained through the sensing unit.

When a predetermined type of touch is received through the display unit, the controller may execute a specific function corresponding to the received touch regardless of operational state of the electronic device.

When an additional touch is not received through the display unit within a predetermined time after the specific function is executed on the basis of the received touch, the controller may terminate execution of the specific function.

The controller may provide a user interface corresponding to the specific function to the display unit, and when a touch through the user interface is not received within a predetermined time after the user interface is performed, the controller may release displaying of the user interface.

Advantageous Effects

The electronic device according to an embodiment of the present disclosure may generate and provide movement data of a user on the basis of data obtained through a sensing unit.

In addition, the electronic device according to an embodiment of the present disclosure may provide an intuitive user environment using a multi-touch received through a display unit supporting a touchscreen function.

Also, the electronic device according to an embodiment of the present disclosure may perform various functions related to other peripheral devices interworking therewith through near-field communication (NFC).

DESCRIPTION OF DRAWINGS

FIGS. 10 through 14 are views illustrating a method for identifying a user of an electronic device.

FIGS. 15 through 20 are views illustrating a display method of the electronic device of FIG. 1.

FIG. 22 is a view illustrating examples of recognizing through a multi-touch in an electronic device according to an embodiment of the present disclosure.

FIGS. 24 through 27 are views illustrating examples of performing the method of driving an electronic device illustrated in FIG. 23.

FIG. 30 is a view illustrating an example of a music search function provided in an electronic device according to an embodiment of the present disclosure.

BEST MODES

The technical object, characteristics, and advantages of the present disclosure will now be more clearly understood from detailed descriptions given below. In what follows, preferred embodiments according to the present disclosure will be given with reference to appended drawings. Throughout the document, the same reference number represents the same component. In the following description, if it is decided that the detailed description of known function or configuration related to the invention obscures the technical principles of the present disclosure, the corresponding description is omitted.

In what follows, a mobile terminal according to the present disclosure will be described in more detail with reference to appended drawings. A suffix such as "module" and "unit" may be assigned or used interchangeably to refer to elements or components. Use of such a suffix herein is merely intended to facilitate description of the specification, and the suffix itself is not intended to give any special meaning or function.

The mobile terminal in this document may include a cellular phone, a smart phone, a notebook computer, a digital broadcasting terminal, personal digital assistants (PDA), a portable multimedia player (PMP), and a navigation terminal; however, the technical scope of the present disclosure is not limited to the terminals above.

The electronic device may be a stationary terminal such as a digital TV or a desktop computer. Also, the electronic device according to an embodiment of the present disclosure may be implemented as a wearable device such as a watch-type device, a necklace-type device, or a glass-type device.

Figure 1:
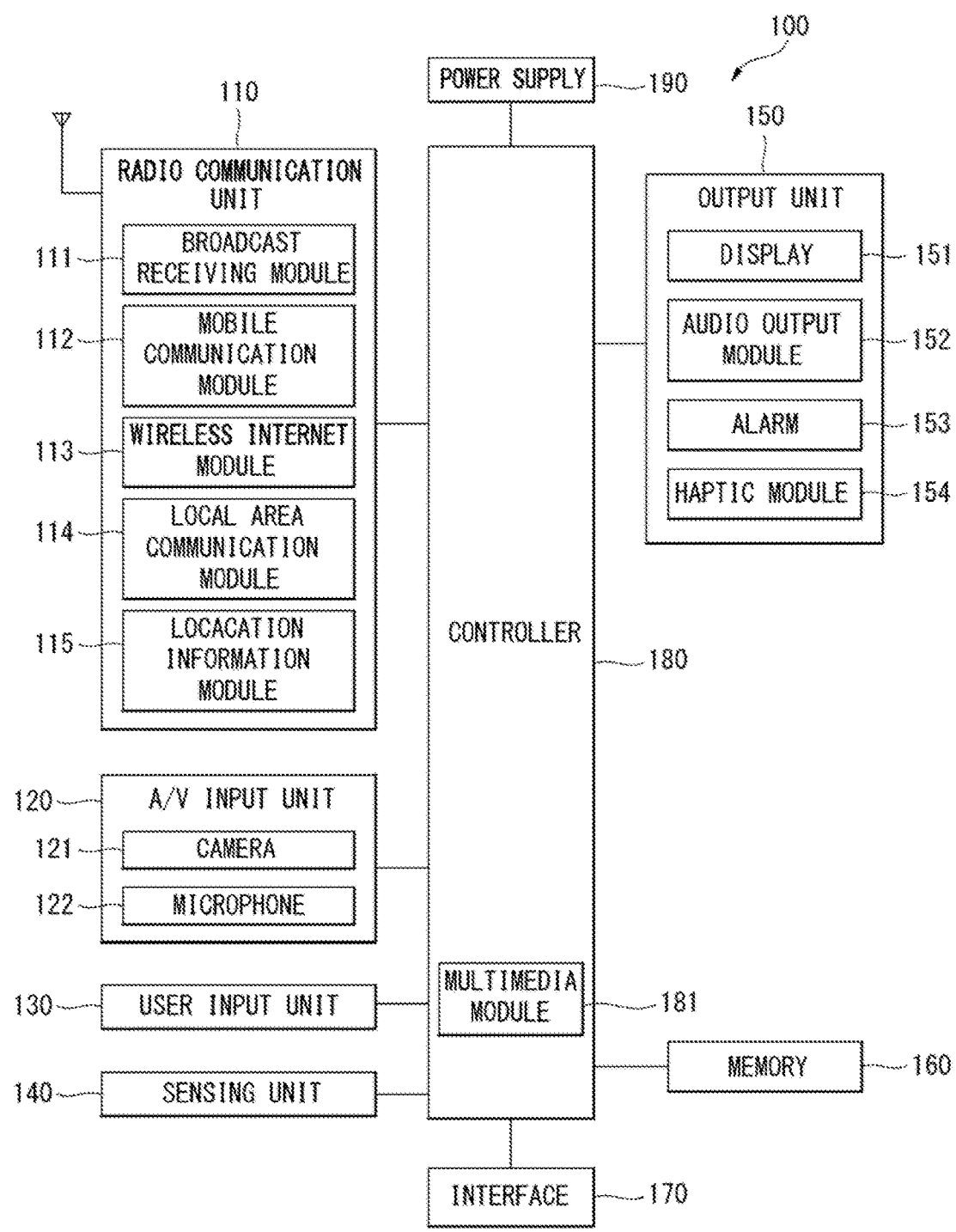
FIG. 1 is a block diagram of an electronic device related to an embodiment of the present disclosure.

FIG. 1 is a block diagram of a mobile terminal according to an embodiment of the present disclosure. With reference to FIG. 1, the mobile terminal 100 comprises a wireless communication unit 110, an Audio/Video (A/V) input unit 120, a user input unit 130, a sensing unit 140, an output unit 150, a memory 160, an interface unit 170, a controller 180, and a power supply unit 190. Although FIG. 1 shows a mobile terminal having various components, it should be understood that implementing all of the illustrated components is not a mandatory requirement; a mobile terminal 100 can be equipped with a larger or smaller number of components than what are shown in FIG. 1.

In what follows, the constituting elements are described one after another.

The wireless communication unit 110 includes one or more components that permit wireless communication between the mobile terminal 100 and a wireless communication system or a network in which the mobile terminal 100 is located. For example, the wireless communication unit 110 includes a broadcast receiving module ill, a mobile communication module 112, a wireless Internet module 113, a short-range communication module 114 and a position information module 115.

The broadcast receiving module 111 receives a broadcast signal and/or broadcast-related information from an external broadcast managing server via a broadcast channel.

The broadcast channel may include a satellite channel or a terrestrial channel or both. The broadcast managing server may refer to a server that generates and transmits broadcast signals and/or broadcast-related information or a server receiving previously generated broadcast signals and/or broadcast-related information and transmitting the broadcast signals and/or the broadcast-related information to the mobile terminal 100. The broadcast signal may include not only a TV broadcast signal, radio broadcast signal, and data broadcast signal, but also a broadcast signal in the form of a TV broadcast signal or a radio broadcast signal combined with a data broadcast signal.

The broadcast-related information may refer to the information about a broadcast channel, a broadcast program, or a broadcast service provider. The broadcast-related information may even be provided over a mobile communication network. In the latter case, the broadcast-related information may be received via the mobile communication module 112.

The broadcast-related information can be realized in various ways. Examples of broadcast-related information include an electronic program guide (EPG) of digital multimedia broadcasting (DMB) and an electronic service guide (ESG) of digital video broadcast-handheld (DVB-H).

The broadcast receiving module 111 receives broadcast signals through various types of broadcast systems. As a non-limiting example, the broadcast systems include digital multimedia broadcasting-terrestrial (DMB-T), digital multimedia broadcasting-satellite (DMB-S), media forward link only (MediaFLO), digital video broadcast-handheld (DVB-H), and integrated services digital broadcast-terrestrial (ISDB-T). The broadcast receiving module 111 may also receive multicast signals. The broadcast receiving module 111 can be configured to be suitable not only for the digital broadcast system described above but also for other types of broadcast systems providing broadcast signals.

The broadcast signals and/or the broadcast-related information received by the broadcast receiving module 111 may be stored in the memory 160.

The mobile communication module 112 transmits and receives radio signals to and from at least one of a base station, an external terminal or a server over a mobile communication network. The radio signals may include voice call signals, video telephony call signals or data in various forms according to the transmission and reception of text and/or multimedia messages.

The wireless Internet module 113 refers to a module intended for wireless Internet access. This wireless Internet module 113 may be internally or externally coupled to the mobile terminal 100. Suitable technologies for wireless Internet include, but are not limited to, WLAN (Wireless LAN), Wi-Fi, Wireless broadband (Wibro), World Interoperability for Microwave Access (Wimax), High Speed Downlink Packet Access (HSDPA), and Long Term Evolution (LTE).

The short-range communication module 114 facilitates relatively short-range communications. Suitable technologies for short-range communication include, but are not limited to, radio frequency identification (RFID), infrared data association (IrDA), ultra-wideband (UWB), and Zig-Bee.

The position information module 115 identifies or obtains a location of the mobile terminal 100. As a typical example of the position information module 115 is a GPS module. The position information module 115 calculates three-dimensional position information of one location (object) at a particular time point in terms of latitude, longitude, and altitude by using information about distances of the location (object) from at least three satellites and information about the time at which the distances are measured and applying trigonometry to the obtained distance information. In a different implementation, while three satellites are used to calculate position and time information, an auxiliary satellite signal is employed additionally to correct the error in the calculated position and time information. The GPS module continuously calculates a current position in real time and calculates velocity information based on the position information.

With reference to FIG. 1, the audio/video (A/V) input unit 120 is intended to receive an audio or video signal and includes a camera 121 and a microphone 122. The camera 121 processes image frames of still pictures or video obtained by an image sensor in a photographing mode or a video telephony mode. The processed image frames are displayed on a display unit 151.

The image frames processed by the camera 121 may be stored in the memory 160 or transmitted to an external device through the wireless communication unit 110. Two or more cameras 121 can be installed depending on the composition type of the mobile terminal 100.

The microphone 122 receives an external audio signal through a microphone while the mobile terminal 100 is in a phone call mode, a recording mode, or a voice recognition mode. The received audio signal is processed and converted into digital voice data. In the call mode, the processed voice data is transformed into a format suitable for transmission to a mobile communication base station via the mobile communication module 112. Various noise removing algorithms to remove noise generated in the course of receiving the external audio signal can be applied to the microphone.

The user input unit 130 generates input data for the user to control operation of the mobile terminal 100. The user input unit 130 can be composed of a keypad, a dome switch, a touchpad (static pressure or static capacitance), a jog wheel, and a jog switch.

The sensing unit 140 provides status measurements of various aspects of the mobile terminal 100. For example, the sensing unit 140 detects an open/closed state of the mobile terminal 100, position of the mobile terminal 100, presence of a user's contact, a touch operation of the user with respect to a particular part, orientation of the mobile terminal, and acceleration or deceleration of the mobile terminal; and generates a sensing signal for controlling operation of the mobile terminal 100.

For example, in case the mobile terminal 100 is a slide-phone type, the sensing unit 140 can sense whether the slide phone is opened or closed. The sensing unit 140 can also have the function of sensing whether the power supply unit 190 supplies power or not, whether the interface unit 170 is connected to an external device, and so on. Meanwhile, the sensing unit 140 can include a proximity sensor.

The output unit 150 generates output related to visual, auditory, and tactile sense and includes a display unit 151, an audio output unit 152, an alarm unit 153, and a haptic module 154.

The display unit 151 displays information processed by the mobile terminal 100. For example, when the mobile terminal 100 is in a call mode, the display unit 151 may display a user interface (UI) or a graphic user interface (GUI) associated with the call. If the mobile terminal 100 is in a video communication mode or a photograph mode, the display unit 151 may display a captured and/or received picture, a UI, or a GUI.

The display unit 151 includes at least one of a liquid crystal display (LCD), a thin film transistor liquid crystal display (TFT LCD), an organic light-emitting diode (OLED), a flexible display, or a 3-dimensional display.

The display unit 151 may be made of a transparent or light-transmission type material, through which the user can see the surroundings of the mobile terminal 100. This kind of display can be called a transparent display. A transparent LCD is a typical example of the transparent display. The rear structure of the display unit 151 can also be made of the light-transmission type material. Due to this structure, the user can see an object located behind the terminal body through the area occupied by the display unit 151 of the terminal body.

At least two or more display units 151 may be provided depending on the implementation type of the mobile terminal 100. For example, a plurality of display units 151 may be disposed on a single surface of the mobile terminal 100 spaced apart from each other or built into a single body.

Alternatively, each of a plurality of display units 151 may be disposed on different surfaces of the mobile terminal 100

If the display unit 151 and a sensor for detecting a touch action (hereinafter, it is referred to as a touch sensor) are constructed to form a mutual-layered structure (hereinafter, it is referred to as a touchscreen), the display unit 151 may be used as an input device as well as an output device. The touch sensor may be constructed in the form of a touch film, a touch sheet, or a touchpad.

The touch sensor can be configured to convert a pressure applied to a specific portion of the display unit 151 or a variation of electrostatic capacity generated at a specific portion of the display unit 151 to an electric input signal. The touch sensor can be configured to detect a pressure at the time of a touch input as well as the position and the area of the touch input.

If a touch input is applied to the touch sensor, a signal(s) corresponding to the touch input is transferred to a touch controller. The touch controller processes the signal(s) and then transfers corresponding data to the controller 180. The controller 180 is then determines which portion of the display unit 151 has been touched.

A proximity sensor can be disposed in an inside area of the mobile terminal enclosed by the touchscreen or around the touchscreen. The proximity sensor refers to a sensor capable of detecting presence or non-presence of an object approaching a specific detecting surface or an object located around the proximity sensor by using electromagnetic field strength or infrared rays without employing a mechanical contact. Accordingly, the proximity sensor exhibits greater durability and greater utility than a contact type sensor.

Examples of the proximity sensor include a transmissive photoelectric sensor, a direct reflective photoelectric sensor, a mirror reflective photoelectric sensor, a high frequency oscillation proximity sensor, an electrostatic capacity proximity sensor, a magnetic-type proximity sensor, and an infrared proximity sensor.

If the touchscreen is an electrostatic type touchscreen, the proximity sensor detects an approach of the cursor by using a variation of an electric field according to the approach of the cursor. In this case, the touchscreen (touch sensor) can be classified as a proximity sensor.

Hereinafter, for the purposes of description, the term "proximity touch" will often be referred to herein to denote the scenario in which a pointer is positioned to be proximate to a touchscreen without contacting the touchscreen. The term "contact touch" will often be referred to herein to denote the scenario in which a pointer makes physical contact with the touchscreen. For the position corresponding to the proximity touch of the pointer relative to the touchscreen, such position will correspond to a position where the pointer is perpendicular to the touchscreen.

The proximity sensor senses a proximity touch and a proximity touch pattern (for example, proximity touch distance, proximity touch direction, proximity touch speed, proximity touch duration, proximity touch position, and proximity touch movement state). Information corresponding to the sensed proximity touch action and proximity touch pattern can be displayed on the touchscreen.

The audio output unit 152 may output audio data received from the wireless communication unit 110 in a call-receiving mode, a communication mode, a recording mode, a voice recognition mode, or a broadcast receiving mode. The audio output unit 152 may also output audio data stored in the memory 160. The audio output unit 152 outputs an audio signal related to a function (for example, a call signal receiving sound, a message receiving sound, and so on) performed by the mobile terminal 100. The audio output unit 152 includes a receiver, a speaker, or a buzzer. Also, the audio output unit 152 can output a sound through an earphone jack 116. The user can listen to an output sound by connecting an earphone to the earphone jack 116.

The alarm unit 153 outputs a signal for notifying occurrence of a particular event associated with the mobile terminal 100. Typical events include a call signal reception, a message reception, a key signal input, and a touch input. The alarm unit 153 may employ a different type of a signal rather than a video or an audio signal, for example, a signal for notifying occurrence of an event by using vibration. The video or audio signal can also be output through the display unit 151 or the audio output unit 152.

The haptic module 154 generates various tactile effects that can be sensed by the user. Vibration is a representative tactile effect generated by the haptic module 154. The haptic module 154 can control the strength and the pattern of a vibration generated. For example, different vibrations can be synthesized or can be output one after another The haptic module 154 can generate various haptic effects in addition to vibration. For example, the haptic module 154 can generate an effect caused by a pin array vertically moving against skin being touched, an effect caused by an air injection force via an injection hole, an effect caused by an air suction force via a suction hole, an effect caused by a stimulus input skimming on a skin surface, an effect caused by a contact with an electrode, an effect caused by electrostatic force, or an effect caused by realizing a hot or cold sense using an endothermic or exothermic device.

The haptic module 154 can be configured to provide a haptic effect via direct contact. The haptic module 154 can also be configured to enable the user to experience the haptic effect via muscular sense of a finger or an arm of the user. Two or more haptic modules 154 can be installed according to a structure of the mobile terminal 100.

The memory 160 stores programs for operation of the controller 180 and temporarily stores input/output data (for example, phonebook, message, still picture, moving picture, and the like). The memory 160 can store data about vibration and sound of various patterns output when the user touches the touchscreen.

The memory 160 can include at least one type of storage media from among a flash memory, a hard disk, a multimedia card micro type memory, a card type memory (e.g., SD memory, XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The mobile terminal 100 can operate in association with a web storage that performs a storage function of the memory 160 on the Internet.

The interface unit 170 performs the role of a passage to all kinds of external devices connected to the mobile terminal 100. The interface unit 170 receives data or power from an external device and delivers the received data or power to individual elements within the mobile terminal 100. The interface unit 170 may be configured to transfer data from the mobile terminal 100 to an external device.

For example, the interface unit 170 may include a wired/wireless headset port, an external charger port, a wired/wireless data port, a memory card port, a port for coupling the mobile terminal 100 to a device having an identity module, an audio input/output (I/O) port, a video input/output (I/O) port, and an earphone port.

An identification module, a chip that stores various types of information for authenticating authority to use the electronic device 100, may include a user identity module (UIM), a subscriber identity module (SIM), a universal subscriber identity module (USIM), and the like. In addition, a device having the identification module (hereinafter, referred to as an "identifying device") may take the form of a smart card. Accordingly, the identifying device may be connected to the terminal 100 through a port.

The interface unit 170 can include a card slot into which a user identification module (UIM) of the card type can be installed. Then the user identification module can be connected to the mobile terminal 100 through the card slot. At this time, a plurality of user identification modules can be connected to the interface unit 170.

The interface unit 170 can be configured to perform as a passage for supplying power to the mobile terminal 100 when the mobile terminal 100 is connected to an external cradle. Also, various command signals input through the cradle by the user can be delivered to the mobile terminal through the interface unit 170. Various command signals or power input through the cradle can be used to indicate that the mobile terminal has been correctly loaded into the cradle.

The controller 180 typically controls the overall operation of the mobile terminal 100. For example, the controller 180 performs control and processing related to voice calls, data communication, and video calls. The controller 180 may include a multimedia module 181 meant for play of multimedia contents. The multimedia module 181 can be implemented inside the controller 180 or separately from the controller 180.

The controller 180 can perform a pattern recognition process for recognizing a handwriting input or a drawing input on the touchscreen as a character or an image.

The power supply unit 190 receives internal and external power by the control of the controller 180 and provides power required for operation of various components for the mobile terminal 100.

Various embodiments of the present disclosure described in this document can be implemented within a recording medium that can be read by a computer or a device similar thereto by using software, hardware, or a combination thereof.

As for hardware implementation, embodiments of the present disclosure can be implemented by using at least one of application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, and electrical units for performing functions. In some cases, the embodiments may be implemented by the controller 180.

In the case of software implementation, embodiments of the present disclosure related to a procedure or a function can be implemented with a separate software module which enables at least one function or operation to be carried out. Software codes may be implemented by a software application written in a suitable programming language. Also, the software codes can be stored in the memory 160 and executed by the controller 180.

Figure 2:
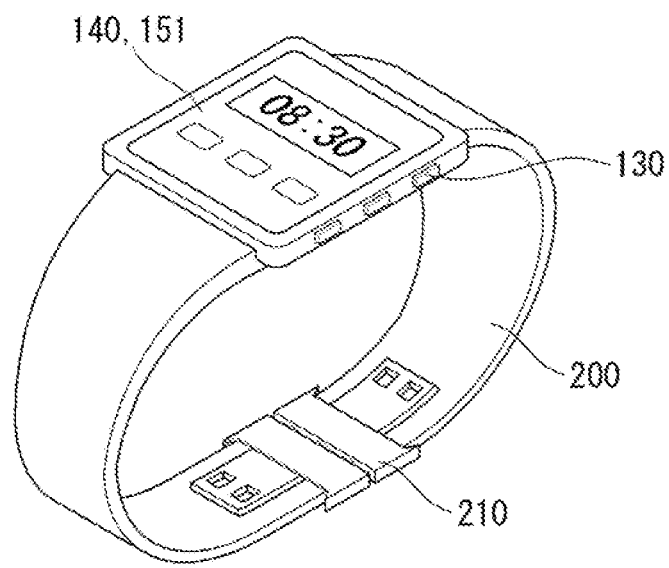
FIG. 2 is a perspective view illustrating an external appearance of an electronic device having a wearable band according to an embodiment of the present disclosure.

FIG. 2 is a perspective view illustrating an example of an external appearance of the electronic device 100 having a wearable band.

Referring to FIG. 2, the electronic device 100 may include a small body in which a portion or the entirety of the components of FIG. 1 is integrated, a band 200 connected to both ends of the small body, and a unit 210 (for example, a buckle) for fastening the band. On a front surface of the small body, a display screen of the display module 151 may be installed and a touchscreen of the sensing unit 140 installed within the display screen or mounted on the display screen may be disposed. On a side surface of the main body, an input means of the input unit 130, for example, a keypad, a touchpad, or any other input means, may be disposed. In addition for an antenna for mobile communication, an antenna for receiving a broadcast signal may be disposed on the side surface of the small body, and the antenna(s) may be installed to be drawn out from the small body.

The band 200 and the buckle 210 serves to fix the small body of the electronic device 100 to a user's wrist, like a wristwatch. The band 200 may be formed of a synthetic resin, a metal, a natural/artificial leather material, or a highly elastic material, or any combinations thereof. Also, the buckle 210 may be formed of a metal.

Figure 3:
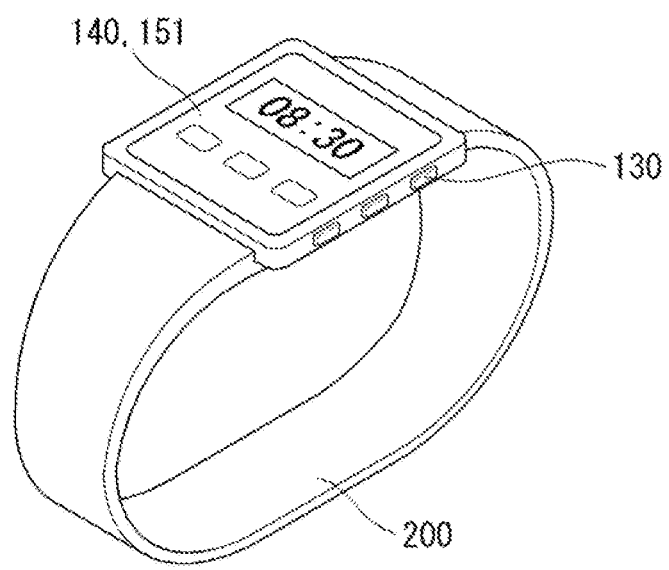
FIG. 3 is a perspective view illustrating a different external appearance of an electronic device having a wearable band according to an embodiment of the present disclosure.

Referring to FIG. 3, in a case in which the band 200 is formed of a material having high elasticity, the buckle 210 may be omitted. In this case, due to elasticity of the band 200, when the user pulls the band 200 to the vicinity of the wrist, a width and an overall length of the band 200 may be lengthened, unlike a case in which the user wears the electronic device 100 near the wrist.

The electronic device 100 may be manufactured to have a special structure like a configuration of a wristwatch as illustrated in FIGS. 2 and 3, but the present disclosure is not limited thereto and the electronic device 100 may be implemented to have various structures such as an existing bar type or a slide type, a folder type, a swing type, or a swivel type in which two or more bodies are coupled to be relatively movable.

In the electronic device 100 having the wearable band to which the present disclosure is applied, the band may be variously modified to be implemented, without being limited to the aforementioned buckle type band, or a band formed of a material which extends or contracts by a predetermined range.

For example, the band of the electronic device according to an embodiment of the present disclosure may be integrally provided in the display unit 151 of the electronic device and may include a first band part which is connected to one end of the display unit 151 and extends therefrom and a second band part which is connected to the other end of the display unit 151 and extends therefrom. Here, the first band part and the second band part may not be connected to each other. That is, when the user wears the electronic device on his or her wrist, there may be a predetermined gap between the first band part and the second band part.

As described above, the configuration of the electronic device to which the present disclosure is applied is not limited to the example illustrated in FIGS. 2 and 3.

Figure 4:
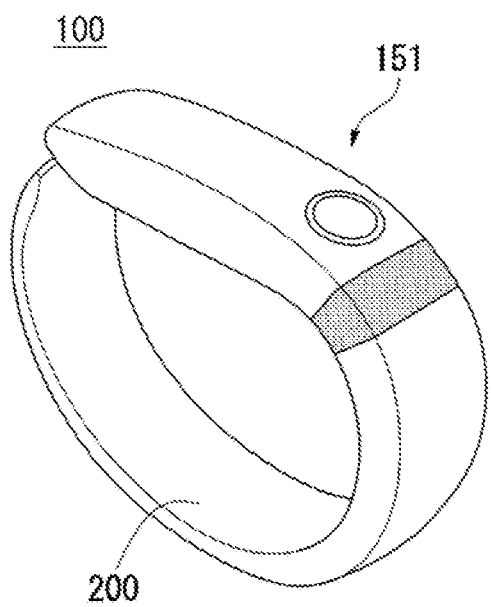
FIG. 4 is a perspective view another embodiment of the electronic device of FIG. 1.
Figure 5:
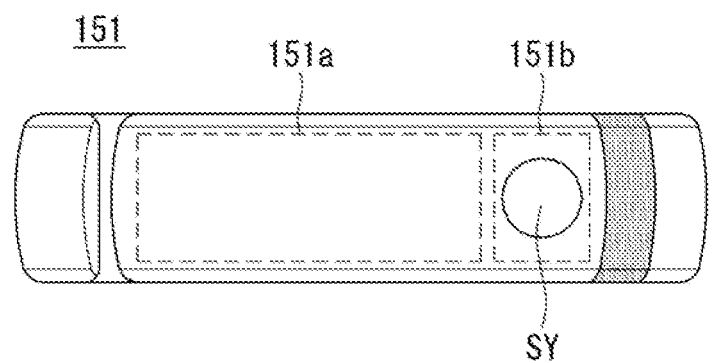
FIG. 5 is a view illustrating a display of the electronic device of FIG. 4.

FIG. 4 is a perspective view of the electronic device of FIG. 1 according to another embodiment, and FIG. 5 is a view illustrating a display of the electronic device of FIG. 4.

As illustrated in FIGS. 4 and 5, the electronic device 100 according to another embodiment of the present disclosure may include a display unit 151 and a band 200 worn on the user's wrist.

The display unit 151 may include a content display region 151a and an indicating region 151b. The content display region 151a and the indicating region 151b may be formed to be continuous such that the mutual regions may not be apparent externally. That is, a visual effect that the content display region 151a and the indicating region 151b appear to be a single region when the display unit 151 does not operate is obtained. Since the effect that the content display region 151a and the indicating region 151b are a single region is obtained, an external appearance of the electronic device 100 may become finer.

A function executed in the electronic device 100 may be displayed and/or a character, a number, or a symbol related to selection of a function may be displayed in the content display region 151a. The content display region 151a will be described in detail in a relevant part hereinafter.

A state of the electronic device and/or the user may be displayed in the indicating region 151b. For example, a circular symbol SY may be displayed in the indicating region 151b. The symbol SY may have a color changed according to a state of the electronic device and/or the user and/or may blink. For example, the symbol SY may be expressed in different colors according to a target exercise amount of the user and an exercise amount up to the present. The symbol SY may be displayed differently according to a current state of the electronic device 100. For example, the symbol SY may be expressed in a green color in a normal mode, in a yellow color in an exercise mode, or in a red color in a sleep mode. When the electronic device 100 is paired or in sync with a different electronic device including a user's mobile terminal, the symbol SY may be displayed or blink in a specific color.

The band 200 may be a part extending from the display unit 151 and coupled to the user's wrist. The band 200 may have a predetermined level of elasticity so as to be naturally worn on the user's wrist. A tensile sensor capable of sensing a degree of extending or contracting may be provided in the band 200 and/or the main body of the electronic device 10. A thickness of the user's wrist that wears the electronic device 100 may be measured through the tensile sensor. A temperature sensor may be provided in the band 200 and/or the main body of the electronic device 100. A body temperature of the user who wears the electronic device 100 and/or an ambient temperature may be measured through the temperature sensor. An accelerometer sensing a movement of the electronic device 100 may be provided in the band 200 and/or the electronic device 100. A movement of the user who wears the electronic device 100 may be measured through the accelerometer. A position module sensor sensing a position of the electronic device 100 may be provided in the band 200 and/or the main body of the electronic device 100. A current position and/or an altitude of the electronic device 100 may be sensed through the position module sensor.

Figure 6:
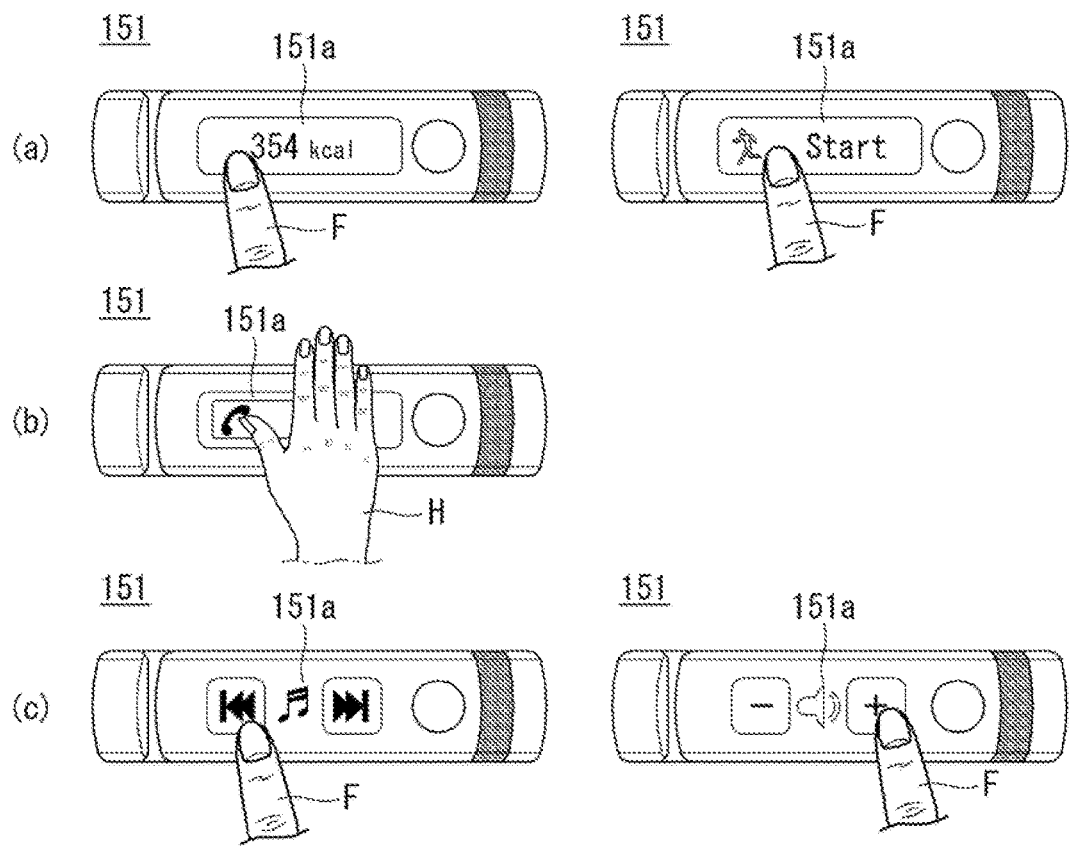
FIGS. 6 and 7 are views illustrating display aspects of the display of FIG. 5.
Figure 7:
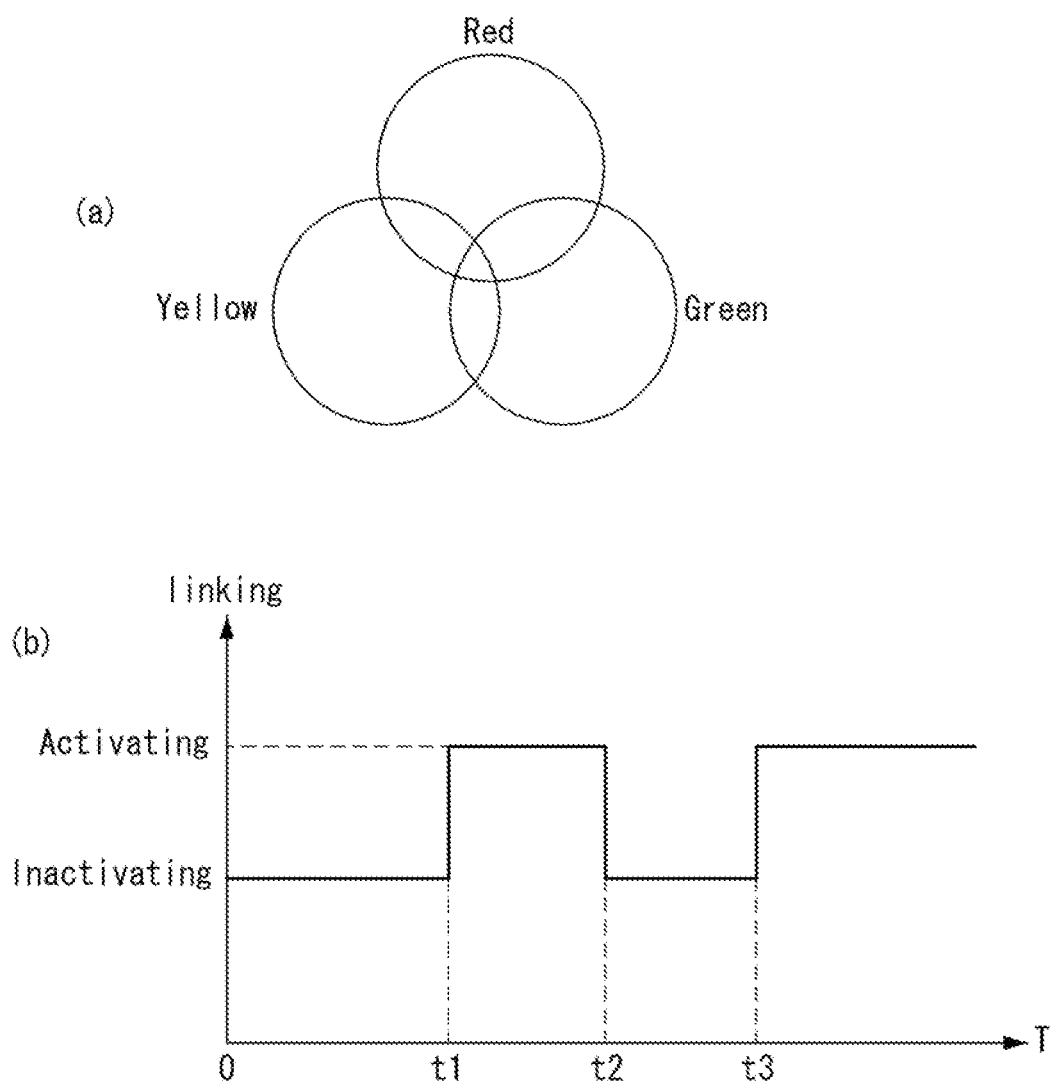

FIGS. 6 and 7 are views illustrating a display aspect of the display of FIG. 5.

As illustrated in FIGS. 6 and 7, the display 151 of the electronic device 100 according to an embodiment of the present disclosure may display information required for the user using the content display region 151a and the indicating region 151b. Also, a user manipulation may be received through at least one of the two regions.

As illustrated in (a) of FIG. 6, in response to a touch operation using a finger F, or the like, with respect to the content display region 151a, the controller 180 may sequentially change display information of the content display region 151a. For example, when a user's touch applied to the content display region 511a is sensed in a state in which user's consumed calories are displayed, the controller 180 may change display of the content display region 151a to display a menu allowing for selection of stop/start of a function. Display information that may be displayed on the content display region 151a may include, for example, A to E. The controller 180 may change display information in order of A→B→C→D→E in response to the user's touch operation.

As illustrated in (b) of FIG. 6, a user's touch operation with respect to the content display region 151a may be a multi-touch operation including a palm touch using the entire palm H. When the palm touch is applied to the content display region 151a, the controller 180 may generate a control signal different from that of a touch using a finger F applied to a specific spot. For example, if a function of sequentially changing display information is executed when a touch using a finger F is applied, a specific function such as making a phone call may be immediately executed when the palm touch using the palm H is applied.

As illustrated in (c) of FIG. 6, when a user's touch is applied to a specific portion of the content display region 151a, the controller 180 may execute a function corresponding to the touched region. For example, when the user touches a fast forward button or rewind button with his or her finger F, or the like, while music is being played, a corresponding function may be executed. Alternatively, when the user touches a specific region while a volume control function is being executed, the volume may be turned up or down As illustrated in FIG. 7, the electronic device 100 according to an embodiment of the present disclosure may change display of the indicating region 151b in various manners.

As illustrated in (a) of FIG. 7, the symbol SY displayed in the indicating region 151b may be displayed in a color obtained by combining at least one of red, yellow, and green according to circumstances. For example, the symbol SY may be displayed in red in a specific situation, and when the circumstance is changed, the symbol SY may be displayed in yellow. Since the color is changed according to circumstances, the user may recognize a current state by intuition upon seeing only the color of the content display region 151a. That is, as described above, the symbol SY may be changed in color according to a specific operation mode such as the normal mode, the exercise mode, and the sleep mode as described above.

As illustrated in (b) of FIG. 7, the symbol of the indicating region 151b may blink according to circumstances. For example, a blinking function may be deactivated up to a point in time t1, and the symbol SY may blink from the point in time t1 to a point in time t2. Also, the symbol SY may not blink from the point in time t2 to a point in time t3, and may blink from the point in time t3. Blinking of the symbol SY may be performed in a preset specific situation that the electronic device 100 is connected to a different device or that the electronic device 100 is being charged.

Blinking of the symbol SY and a change in color of the symbol SY may be combined to be executed. For example, even when the symbol SY is red, the symbol SY may blink or may not blink. Thus, various types of information may be displayed by the symbol SY in the limited region.

Figure 8:
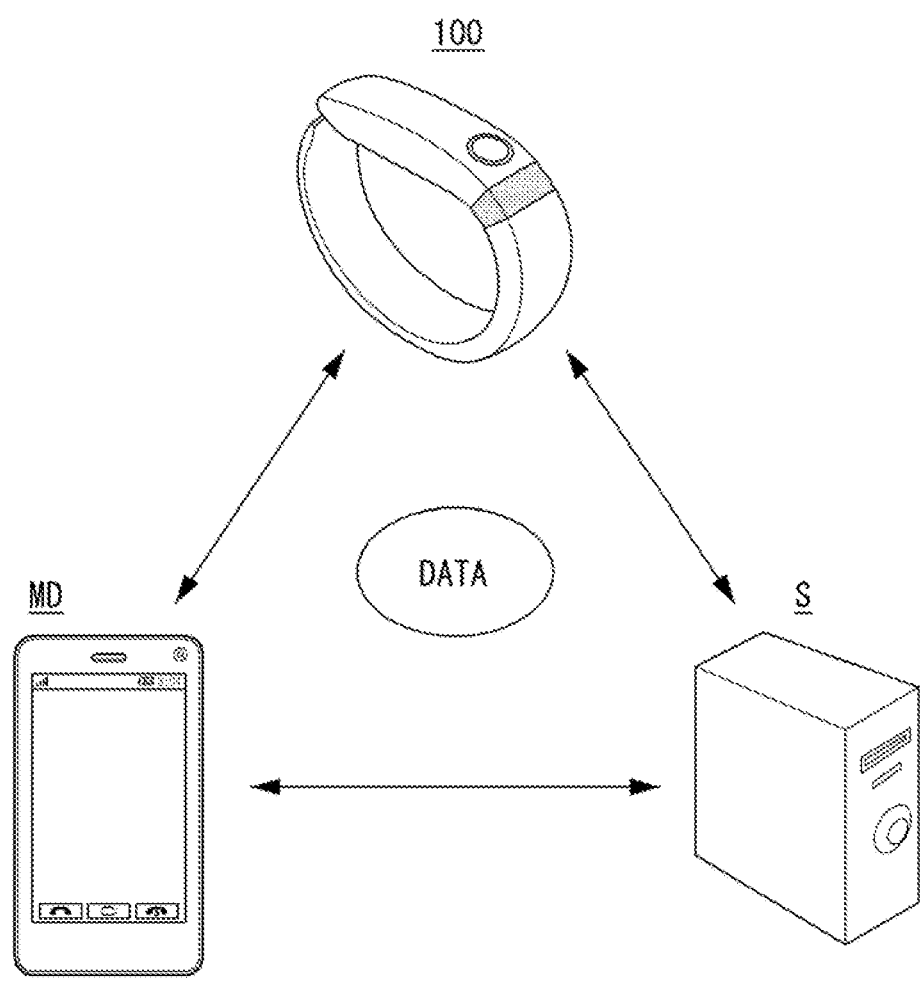
FIG. 8 is a view illustrating an operation of the electronic device of FIG. 4.

FIG. 8 is a view illustrating an operation of the electronic device of FIG. 4.

As illustrated in FIG. 8, the electronic device 100 according to an embodiment of the present disclosure may exchange data with a mobile terminal (or a mobile device (MD)) and/or a server S.

The electronic device 100 may collect various types of data through at least one of the tensile sensor, the temperature sensor, the accelerometer, and the position module sensor. That is, the electronic device 100 may collect data related to movement of the user who wears the electronic device 100 and/or a change in a physical condition.

The data collected through the electronic device 100 may be transmitted to the mobile terminal MD. The data transmitted to the mobile terminal MD may be classified by specific users or operation modes so as to be stored.

The mobile terminal MD may transmit data obtained from the electronic device 100 to the server S. Also, the mobile terminal MD may transmit predetermined data to the electronic device 100. For example, the mobile terminal MD may transmit basic information identifying a specific user to the electronic device 100. Upon receiving the basic information, the electronic device 100 may identify the user who wears the electronic device 100. For example, when a movement pattern of each of specific users is received from the mobile terminal MD, the electronic device 100 may compare the received data with a current movement pattern to determine who is the user that currently wears the electronic device 100, even without a separate input. The user may be identified by at least any one of the electronic device 100, the mobile terminal MD and/or the server S on the basis of the obtained data.

The server S may obtain data from the mobile terminal MD and/or the electronic device 100. For example, in a case in which the electronic device 100 is accessory equipment of the mobile terminal MD, the mobile terminal MD may serve as a relay between the electronic device 100 and the server S. In a case in which the electronic device 100 is able to communicate with the exterior alone, the electronic device 100 may directly transmit data to the server S.

The server S may generate user identification information, or the like, on the basis of the data obtained from the mobile terminal MD and/or the electronic device 100. For example, the server S may derive characteristics of each user by analyzing the large amount of data obtained from the electronic device 100. In the aspect of system resource, the server S may advantageously analyze the data, compared with the electronic device 100 or the mobile terminal MD.

Figure 9:
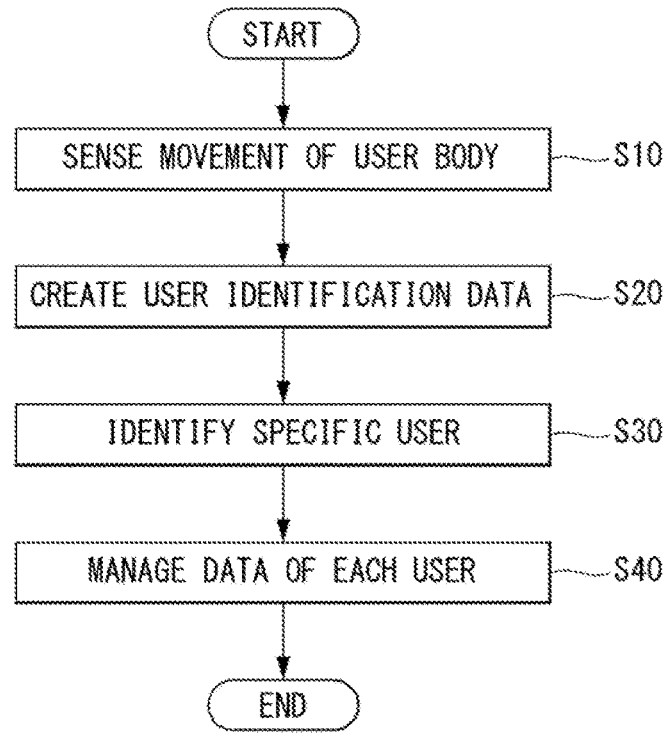
FIG. 9 is a flow chart illustrating an operation of the electronic device of FIG. 1.

FIG. 9 is a flow chart illustrating an operation of the electronic device of FIG. 1.

As illustrated in FIG. 9, a controller 180 of the electronic device 100 according to an embodiment of the present disclosure may detect movement of the user's body (S10).

The electronic device 100 may include a sensing unit 140 sensing movement of the user's body that wears the electronic device 100. For example, the electronic device 100 may include an accelerometer and/or a position module sensor. When the electronic device 100 in the form of a watch-type watch phone is worn on the wrist, the sensing unit 140 may sense movement of the user substantially in real time. That is, the sensing unit 140 may sense movement of the user, and the like, the moment the user puts on the electronic device 100. For example, when it is determined that the user who wears the electronic device 100 stands, the electronic device 100 may obtain data for estimating the user's height through a position of the user's wrist. Also, when the user waves his or her arms to walk, the electronic device 100 may obtain data related to at least one of a period at which the user's arms are waved, a change in a height of the waved arms, and a unique pattern of the waved arms.

User identification data may be created (S20).

The user identification data may be created on the basis of the data obtained through the sensing unit 140. For example, as described above, at least one data among the data related to the user's height, the period at which the user's arms are waved, the change in a height of the waved arms, and the unique pattern of the waved arms may be unique identification data of each person. That is, the foregoing data may be different according to heights of persons, lengths of arms of persons, gait habits of persons. Thus, user identification data may be created on the basis of the foregoing data.

A specific user may be identified (S30).

The user identification data may be data for identifying a user who currently wears the electronic device 100. Also, data of each user of the electronic device 100 may be accumulated on the basis of previous data. Thus, previously accumulated user data may be compared with the user identification data to determine who is the user that currently wears the electronic device 100.

User data is managed (S40).

The data and/or the user identification data obtained through the sensing unit 140 may be stored in the electronic device 100, or the like. The user identification data may be updated through analysis of the stored data, whereby a specific user may be more accurately determined.

FIGS. 10 through 14 are views illustrating a method for identifying a user of the electronic device of FIG. 1.

As illustrated in FIGS. 10 through 14, the electronic device 100 according to an embodiment of the present disclosure may identify a specific user in various manners.

Figure 10:
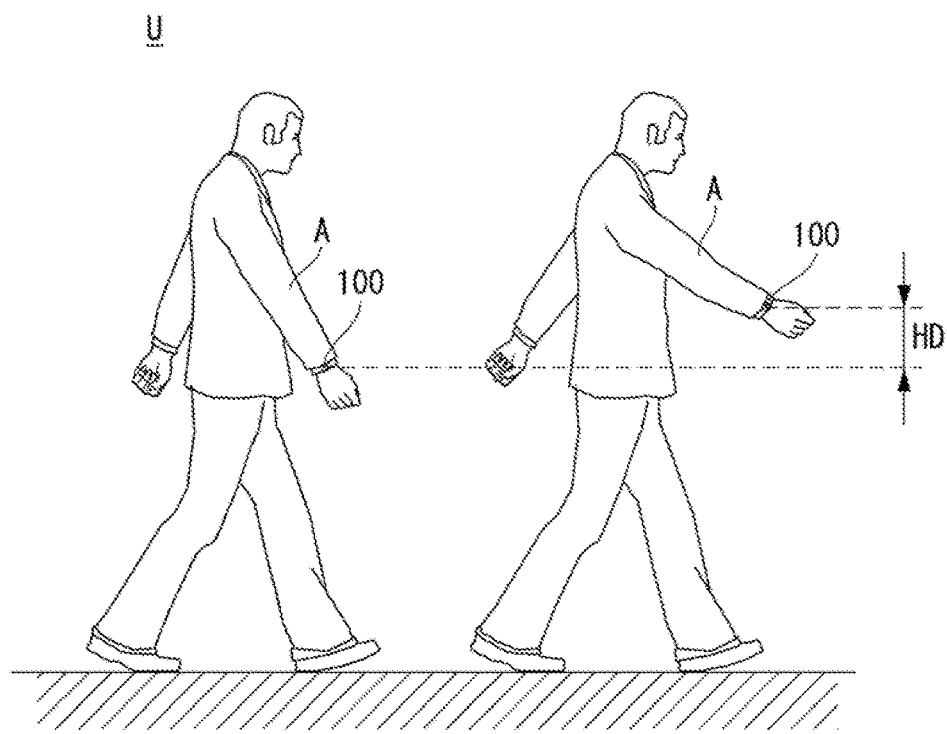

As illustrated in FIG. 10, the sensing unit 140 may sense a movement pattern of the user U who wears the electronic device 100. For example, the sensing unit 140 may estimate the user's height on the basis of a distance from the ground to the electronic device 100. In a statistical access, when a length from the ground to the arm is known, the user's height may be estimated. Alternatively, a specific user who wears the electronic device 100 may be determined on the basis of the length from the ground to the arm that may be different for each user, without estimating the user's height.

In a case in which the user who wears the electronic device 100 moves, the user's arm A may wave at a predetermined period and with a height HD from a lowest point to a highest point. The waving of the user's arm A may be different for each user. For example, a child's arm may rapidly wave at a relatively low height, and an adult's arm may slowly wave at a relatively high height. Thus, the controller 180 may identify the user who wears the electronic device 100 on the basis of movement of the user's arm A sensed through the sensing unit 140, or may collect data required for identification.

Figure 11:
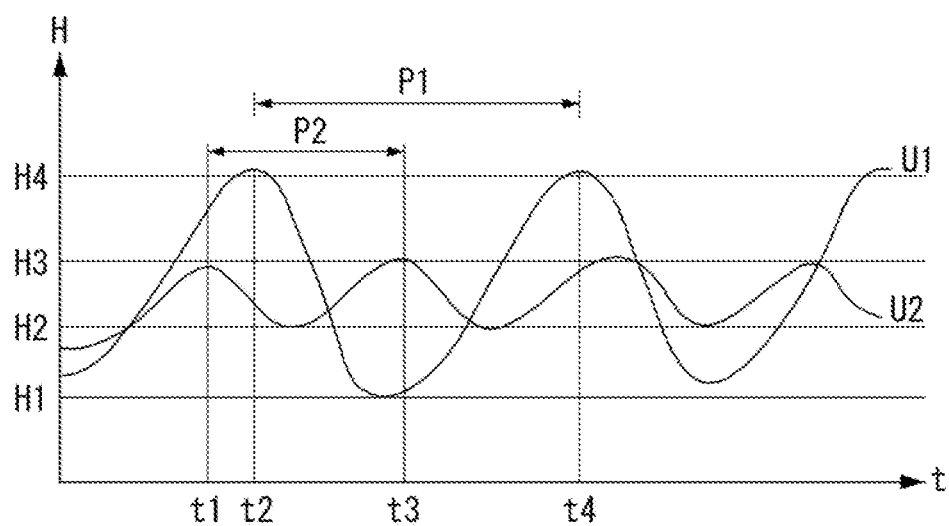

As illustrated in FIG. 11, heights H or periods P1 and P2 at which a first user U1 and a second user U2 wave arms may be different. For example, the first user U1 may wave his or her arm between a lowest point H1 to a highest point H4 at the period of P1, and the second user U2 may wave his or her arm between a lowest point H2 to a highest point H3 at the period of P2. A specific user may be identified on the basis of the periods P1 and P2 and the distance between the lowest point and the highest point.

As illustrated in FIG. 12, a specific user may be identified on the basis of direct physical characteristics of the user who wears the electronic device 100.

As illustrated in (a) of FIG. 12, a thickness of the wrist of a user who wears the electronic device 100 may be W1. The thickness of the user's wrist may be sensed through the band 200 of the electronic device 100. That is, the thickness of the user's wrist may be sensed through the tensile sensor provided in the band 200 and/or the main body of the electronic device 100.

As illustrated in (b) of FIG. 12, a thickness of the wrist of a user who wears the electronic device 100 may be W2. Thicknesses of wrists may be different by users. That is, W1 and W2 may be different. The electronic device 100 and/or a different device which has received data from the electronic device 100 may identify a specific user on the basis of a thickness of a wrist.

The sensing unit 140 may measure a temperature of a user's wrist. Temperatures of wrists may be different by users. The electronic device 100 or a different device which has received data from the electronic device 100 may identify a specific user on the basis of a temperature of a wrist.

As illustrated in FIG. 13, a specific user may be identified according to exercise characteristics of a user.

As illustrated in (a) of FIG. 13, exercise characteristics of users may be different by time zones. That is, exercise patterns including exercise intensities of a first user USER1 and a second user USER2 may be different. For example, the first user USER1 may tend to do exercise with relatively high intensity, while the second user USER2 may tend to do exercise with relatively low intensity. Also, the first user USER1 may tend to have the exercise intensity which is frequently changed during exercise, while the second user USER2 may tend to continuously do exercise with a uniform or like intensity. Exercise characteristics data of each user may be stored in the electronic device 100 and/or the mobile terminal MD. Thus, the electronic device 100 and/or the mobile terminal MD may compare the current exercise intensity data with the exercise characteristics data of each user to determine a user who is wearing the electronic device 100. That is, even though data regarding the current user is not received from the user, the user may be determined.

As illustrated in (b) of FIG. 13, exercise patterns of the users may be different by days. For example, the first user USER1 may tend to do exercise on Sunday, Tuesday, Thursday, and Saturday, while the second user USER2 may tend to do exercise on Sunday, Monday, Wednesday, and Saturday. On the basis of the exercise patterns of the users, the electronic device 100 and/or a different device which has received data from the electronic device 100 may determine who is currently wearing the electronic device 100.

Figure 14:
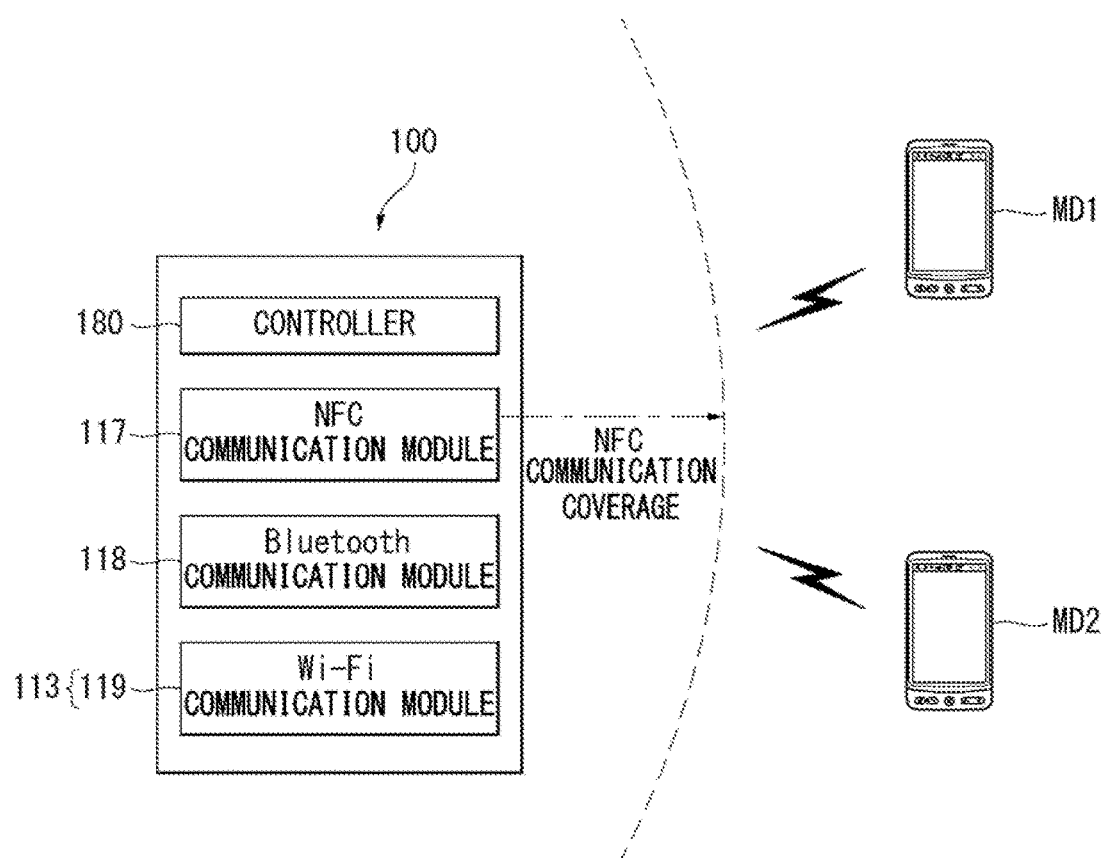

As illustrated in FIG. 14, the electronic device 100 according to an embodiment of the present disclosure may establish a near field communication (NFC) link with at least one mobile terminal MD1 and MD2.

This is not an essential configuration of the aforementioned system environment, and thus, the system environment may include fewer or greater components than those illustrated in FIG. 14. Also, in FIG. 14, components essential for establishing a communication link are briefly illustrated to largely describe features of communication link establishment of the electronic device 100

The electronic device 100 and the mobile terminals MD1 and MD2 may support NFC communication. That is, the electronic device 100 and the mobile terminals MD1 and MD2 may be an electronic device such as a mobile phone, a smartphone, a tablet PC, a printer, a TV, a DTV, a computer, and an audio device. Hereinafter, an electronic device having an NFC communication function may be termed an NFC electronic device.

Also, in FIG. 14, the electronic device 100 may establish an NFC link with the mobile terminals MD1 and MD2 on the basis of NFC communication technology, a sort of short-range communication technology, but the present disclosure is not limited thereto. For example, the electronic device 100 may establish a wireless communication link with the mobile terminals MD1 and MD2 using a short-range wireless communication technology other than the NFC communication technology.

Referring back to FIG. 14, the electronic device 100 includes the controller 180, an NFC communication module 117, a Bluetooth communication module 118, and a Wi-Fi communication module 119.

The controller 180 may control components within the electronic device 100. The NFC communication module 117 may allow the electronic device 100 to establish an NFC link with the mobile terminals MD1 and MD2 supporting NFC communication. The NFC communication module 117 may refer to an NFC forum device. In this document, the NFC communication module may be called a short-range communication unit.

As illustrated in FIG. 14, the NFC communication module 117 may establish an NFC link with NFC communication modules of the mobile terminals MD1 and MD2 within NFC communication coverage through tagging.

The NFC communication module 117 may communicate with the NFC communication modules of the mobile terminals MD1 and MD2 in various modes. For example, the various modes may include a card emulation mode, a reader mode, and a peer-to-peer mode.

In a case in which the NFC communication module 117 operates in the card emulation mode, the NFC communication module 117 of the electronic device 100 may serve as a card, in other words, as a tag. In this case, the NFC communication modules of the mobile terminals MD1 and MD2 may operate in the reader mode to obtain data from the NFC communication module 117 of the electronic device 100.

In a case in which the NFC communication module 117 operates in the reader mode, the NFC communication module 117 of the electronic device 100 may serve as a reader. In this case, the NFC communication module 117 of the electronic device 100 may obtain data from the NFC communication modules of the mobile terminals MD1 and MD2 operating in the emulation mode.

In a case in which the NFC communication module 117 operates in the peer-to-peer mode, the NFC communication module 117 of the electronic device 100 and the NFC communication modules of the mobile terminals MD1 and MD2 may exchange data with each other.

A mode of the NFC communication module 117 may be determined according to a predetermined reference. For example, a mode of the NFC communication module 117 may be set according to a user input or a predetermined algorithm.

After establishing the NFC link with the mobile terminals MD1 and MD2 through the NFC communication module 117, the electronic device 100 may establish a different type of communication link from that of the NFC link through a Bluetooth communication module 118 and/or a Wi-Fi communication module 119. When the different type of communication link is established, the electronic device 100 may continue to perform data communication with the mobile terminals MD1 and MD2 through the Bluetooth communication link and/or the Wi-Fi communication link even though the NFC communication link is cut off.

In this document, the sequential process of forming a different communication link to allow the electronic device 100 to continue to communicate with the mobile terminals MD1 and MD2 using a different wireless communication technology, after the formation of the NFC link, will be referred to as handover.

Referring to FIG. 14, the electronic device 100 according to an embodiment of the present disclosure may know that handover will be performed from the NFC communication link to the Bluetooth communication link or the Wi-Fi communication link, but the present disclosure is not limited thereto. For example, the electronic device 100 may perform handover to various communication links such as a radio frequency identification (RFID) communication link or a wireless gigabit (WiGig) communication link.

Although not shown in FIG. 14, the mobile terminals MD1 and MD2 may include components corresponding to those of the electronic device 100. That is, the mobile terminals MD1 and MD2 may include a control unit, an NFC communication module, a Bluetooth communication module, and a Wi-Fi communication module.

In other words, after establishing an NFC link with the mobile terminals MD1 and MD2, the electronic device 100 may establish a different communication link to perform data communication through handover, and here, after the user easily establishes an NFC link between the electronic device 100 and the mobile terminals MD1 and MD2 through NFC tagging, the user may change a communication means to a substitutive communication link appropriate for a remote area and/or high capacity data transmission, compared with the NFC link.

The electronic device 100 may determine a user of a tagged terminal among the mobile terminals MD1 and MD2 as a user of the current electronic device 100.

FIGS. 15 through 20 are views illustrating a display method of the electronic device of FIG. 1.

As illustrated in FIGS. 15 through 20, the electronic device 100 according to an embodiment of the present disclosure may cause the display unit 151 of the electronic device 100 and/or a different device which has received data from the electronic device 100 to display measured data, and the like.

The electronic device 100 is a watch type device worn on the user's wrist, and thus, an area of the display unit 151 may be relatively small. Thus, data measured in the electronic device 100 may be displayed on a display of a mobile terminal MD. However, unless otherwise mentioned, it is assumed that data measured in the electronic device 100 is selectively displayed on the electronic device 100 and/or the display unit of the mobile terminal MD.

Figure 15:
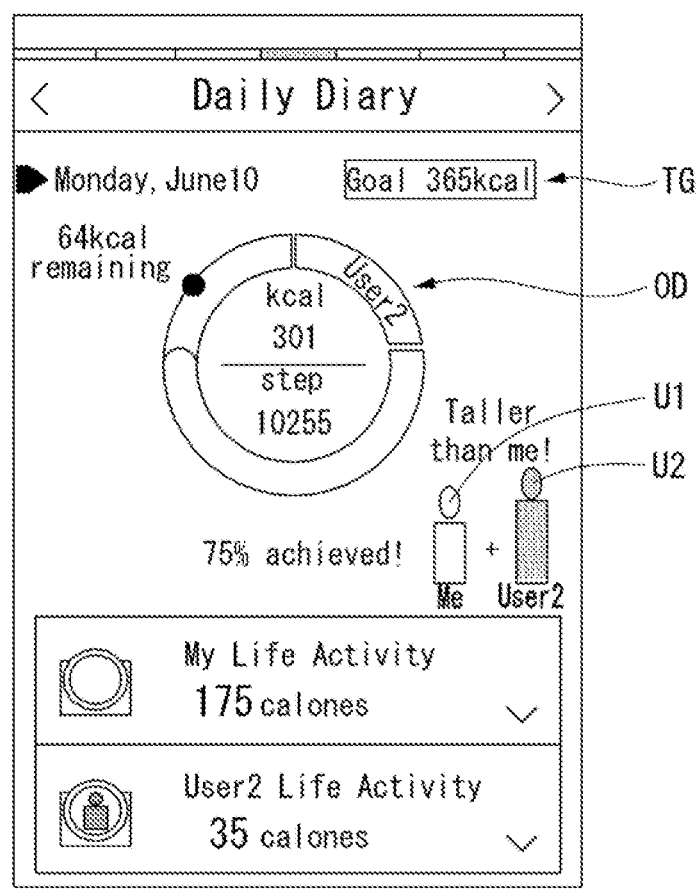

As illustrated in FIG. 15, exercise amounts of users may be displayed on the display unit 151. One of primary functions of the electronic device 100 may be measurement of an exercise amount of a user who wears the electronic device 100. As mentioned above, as soon as the electronic device 100 is worn on the user, the electronic device 100 may measure movement of the user. Also, the electronic device 100 may identify the user who wears the electronic device 100 on the basis of an operational pattern of the user. Thus, the electronic device 100 may measure and display an exercise amount of each user.

The electronic device 100 may visually display a relationship between a first user U1 and a second user U2. For example, an icon representing the first user U1 and an icon representing the second user U2 may be displayed in proportion to heights of the users. Since the icons of the users are displayed in proportion to the heights of the users, a difference between the users may be more intuitively displayed.

The electronic device 100 may display exercise data of each user. For example, the electronic device 100 may display a target amount TG of each user. Also, the electronic device 100 may visually display a current exercise amount graph OD of each user. The current exercise amount graph OD may convert an exercise amount remaining to reach a target amount TG and/or a movement amount of each user into the number of gaits and display the same. An exercise amount of each user may be classified by predetermined periods. For example, the exercise amount of each user may be classified by day, week, and month so as to be displayed and/or stored.

Figure 16:
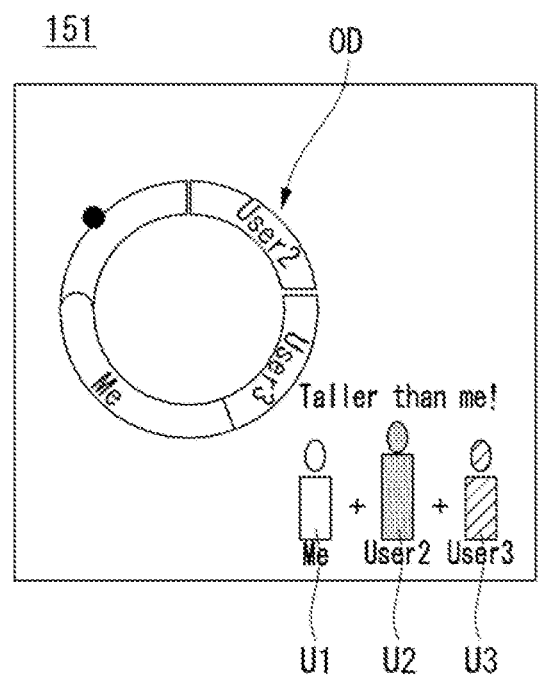

As illustrated in FIG. 16, a movement amount of each user of the electronic device 100 may be visually displayed. For example, sizes of relative builds of first to third users U1 to U3 may be displayed and how much each of the users has done exercise may be expressed intuitively by the current exercise amount graph OD in a circular shape.

As illustrated in (a) of FIG. 17, a user may select the current exercise amount graph OD of a specific user with his or her finger F.

As illustrated in (b) of FIG. 17, when the user touches the current exercise amount graph OD of the specific user, a calorie consumption progress of the user by time may be displayed. Thus, the user may intuitively recognize how much he or she has done exercise in which time zone of a day.

As illustrated in (b) of FIG. 18, when a specific user is selected, an exercise amount of the user may be displayed. For example, types of activity such as daily exercise, walking exercise, running exercise, and climbing exercise may be classified and an exercise amount thereof may be displayed. The types of activity may be sensed through an exercise pattern obtained through the sensing unit 140 of the electronic device 100. This may be clearly understood in consideration of the fact that a daily walking pattern and a running pattern are different.

Figure 19:
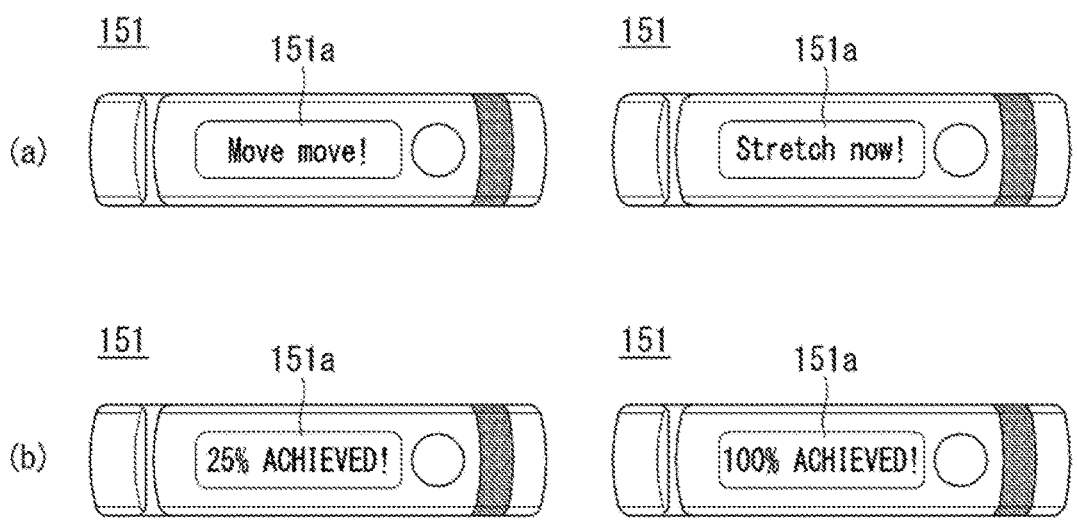

As illustrated in (a) of FIG. 19, a screen urging exercise of the wearer of the electronic device 100 may be displayed in the content display region 151*a*. For example, an encourage message urging the user to move more actively or a message urging the user to make a specific movement may be displayed. When the screen urging exercise is displayed, the audio output module 152 and/or the haptic module 154 included in the electronic device 100 may operate together. That is, it may allow the user to easily recognize that the specific message is displayed.

As illustrated in (b) of FIG. 19, a message of a current exercise amount compared with a target exercise amount may be displayed in the content display region 151*a*.

Figure 20:
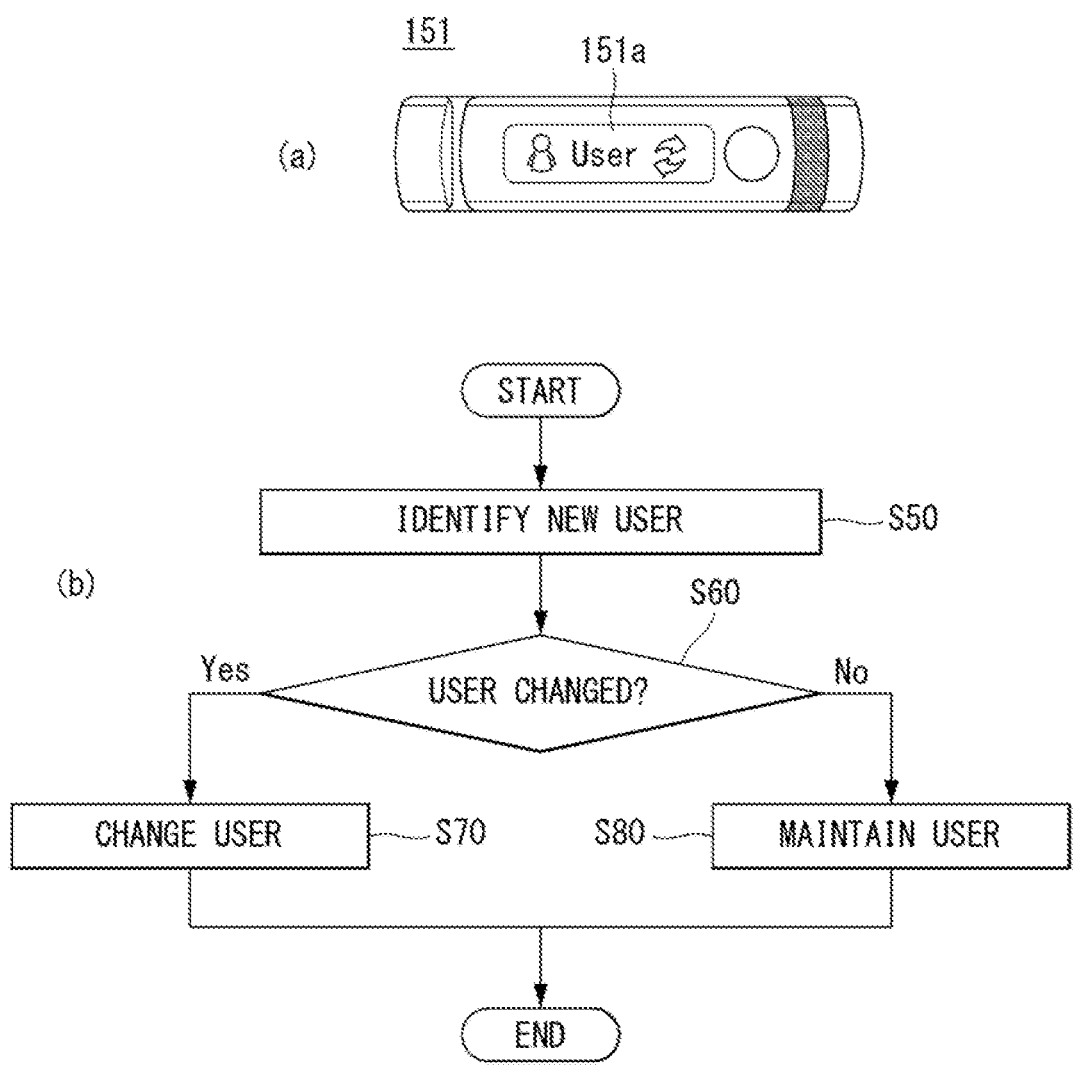

As illustrated in (a) of FIG. 20, when it is determined that the user of the electronic device 100 has been changed on the basis of an exercise pattern, or the like, the electronic device 100 may display the corresponding fact on the content display region 151*a*.

As illustrated in (b) of FIG. 20, a new user of the electronic device 100 is identified (S50). For example, an exercise pattern of the user sensed through the sensing unit 140 may be monitored.

It is determined whether the user has been changed (S60). That is, when the pattern has been changed according to a result of monitoring a usage aspect of the electronic device 100, it may be determined whether the user has been changed.

When it is finally determined that the user has been changed according to the user change determination, the user is changed (S70), and when it is determined that the pattern has been temporarily changed, the user may be continuously maintained (S80). Whether to change the user may be finally selected by the user of the electronic device 100 and/or the mobile terminal MD.

Figure 21:
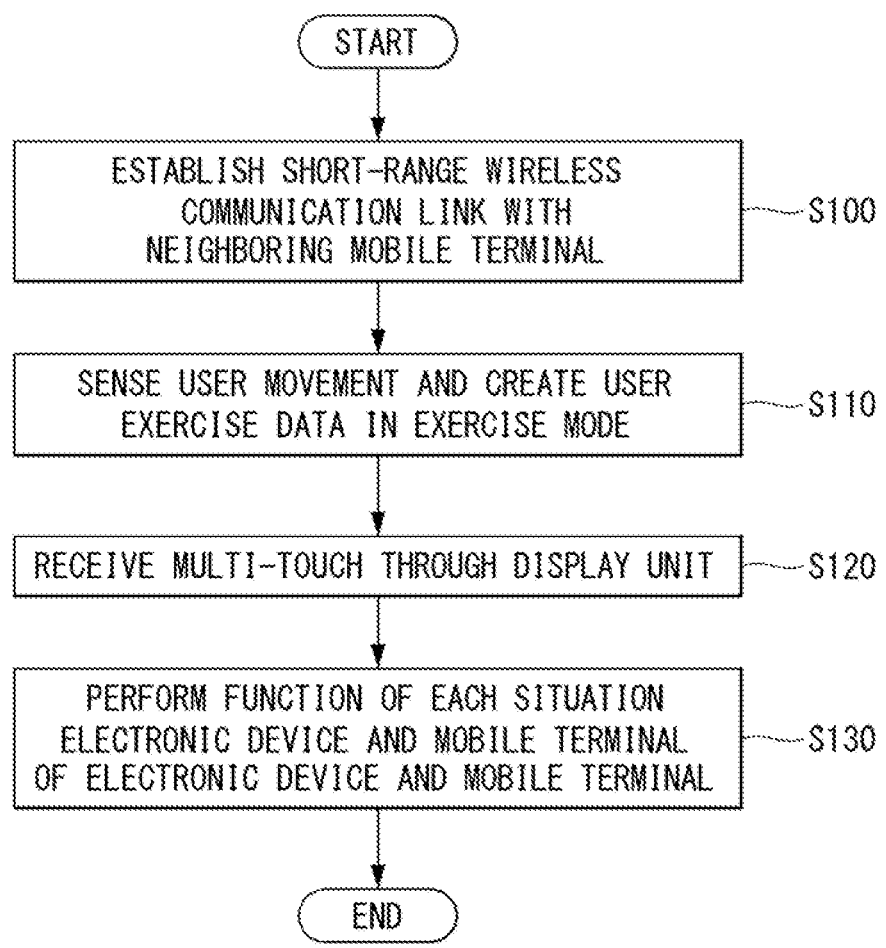
FIG. 21 is a flow chart illustrating another example of a method for driving an electronic device according to an embodiment of the present disclosure.

FIG. 21 is a flow chart illustrating an example of a method of driving an electronic device according to an embodiment of the present disclosure. Hereinafter, the driving method will be described with reference to the relevant drawings.

First, the electronic device 100 establishes a short-range wireless communication link with a mobile terminal therearound (S100). Here, the short-range wireless communication link may be Bluetooth, Wi-Fi, Zigbee, or NFC communication link established by the wireless communication unit 110. However, the scope of the present disclosure is not limited thereto.

Next, when an exercise mode is entered on the basis of user manipulation or data obtained through the sensing unit 140, the controller 180 may sense movement of the user through the sensing unit 140 and creates exercise data of the user on the basis of the sensed movement of the user (S110).

During the performing of the exercise mode, a multi-touch is received through the display unit 151 supporting a touch screen function (S120). Then, the controller 180 performs a function of each situation reflecting an operational state of the electronic device and an operational state of the mobile terminal interworking with the electronic device (S130).

Here, the multi-touch received through the display unit 151 may refer to a touch having a touch area larger than a predetermined width. For example, the multi-touch may include any type of touch whose area is larger than a predetermined area. For example, the multi-touch may be determined on the basis of an area thereof regardless of the number of received touches or position of a touch.

Thus, when the multi-touch is received and the area of the multi-touch is larger than the predetermined area, regardless of a position where the touch has been received or the number of received touches, the electronic device 100 may perform a specific function corresponding to an operational state of the electronic device 100 and an operational state of a peripheral device that interworks with the electronic device 100.

A specific example of a function of each situation performed on the basis of the multi-touch will be described.

First, a function of each situation performed by the multi-touch, reflecting an operational state of the electronic device 100 itself will be described. For example, when a multi-touch is received in a simple exercise mode in which exercise data of a user is created on the basis of data obtained through the sensing unit 140, the electronic device 100 may recognize the multi-touch as a command for terminating the exercise mode. In another example, in a case in which a multi-touch is received while a function of creating exercise data and a function of playing music are simultaneously performed, the controller 180 may perform only a function of stopping playing of music on the basis of the received multi-touch.

Examples of a function of each situation reflecting an operational state of a neighboring electronic device that interworks with the electronic device 100 will be described.

In a case in which a multi-touch is received while a notification operation regarding an event that occurs in the neighboring electronic device is being performed, the controller 180 may perform a response function regarding the event. Such a response function may vary according to types of the generated event.

Meanwhile, in the present disclosure, various embodiments of the present disclosure will be described by taking a mobile terminal, a typical device that may interwork through short-range wireless communication, as an example. However, a peripheral device that may interwork with the electronic device according to an embodiment of the present disclosure is not limited to a mobile terminal. For example, the electronic device 100 may perform various functions by interworking with white home appliances such as a refrigerator or an air-conditioner, as well as a smart TV, a PC, or an audio system.

FIG. 22 is a view illustrating examples of recognizing multi-touches in an electronic device according to an embodiment of the present disclosure.

Referring to (a) of FIG. 22, it can be seen that a multi-touch may be a touch having a large area received by fingers or a palm. Here, the area of the touch may be larger than a predetermined area.

Referring to (b) and (c) of FIG. 22, the multi-touch may be a plurality of touches received at a plurality of positions by a plurality of fingers. Even in this case, however, the sum of the touch areas by the plurality of touches may be larger than the predetermined area.

Even in a case in which the electronic device 100 has an input unit not easy for the user to manipulate, the electronic device 100 according to an embodiment of the present disclosure may provide an intuitive user usage environment that may be instantly handled by situations using an area-based multi-touch.

Figure 23:
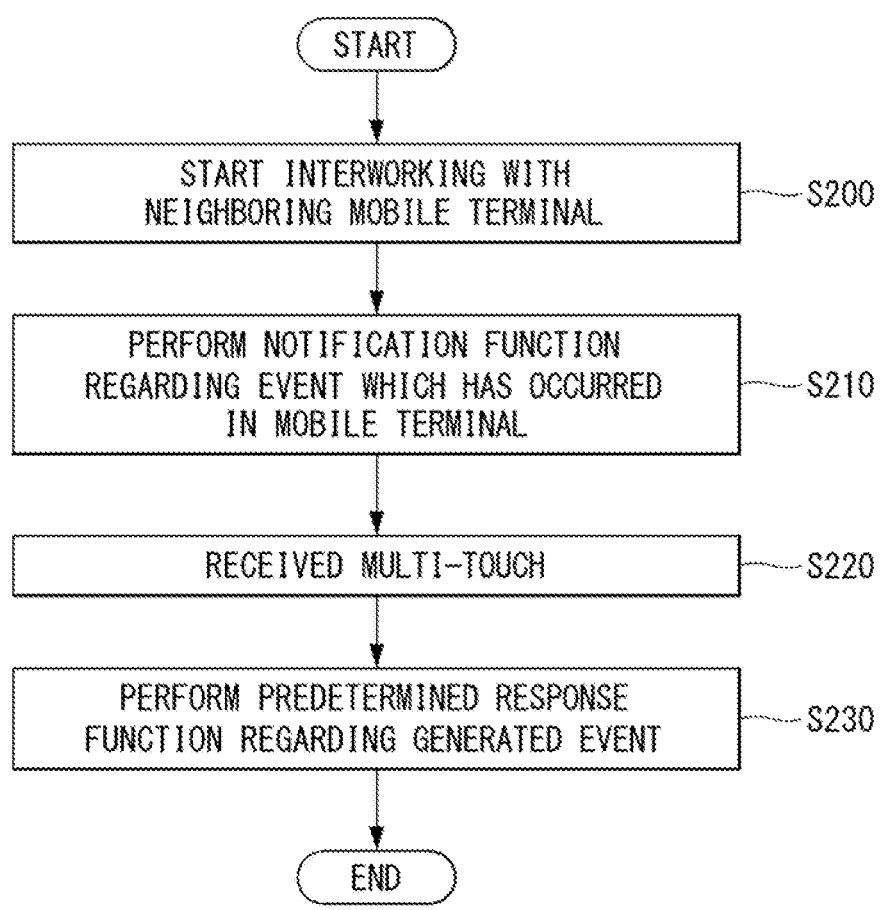
FIG. 23 is a flow chart illustrating another example of a method of driving an electronic device according to an embodiment of the present disclosure.

FIG. 23 is a flow chart illustrating another example of a method of driving an electronic device according to an embodiment of the present disclosure. Hereinafter, the driving method will be described with reference to the relevant drawings.

First, the electronic device 100 starts interworking with a neighboring mobile terminal on the basis of short-range wireless communication (S200). In a state in which the electronic device 100 interworks with the mobile terminal, when an event occurs in the mobile terminal, the controller 180 of the electronic device 100 performs a notification function regarding the event generated in the mobile terminal (S210).

Here, the notification function regarding the event may be performed as providing image information through the display unit 151, providing vibration information through the haptic module 153, and providing sound information through the audio output unit 152 (S210).

For example, the electronic device 100 may vary the form of vibration provided through the haptic module according to events generated in the mobile terminal 300. For example, in a case in which a call reception event occurs in the mobile terminal 300, vibration of 0.5 seconds may be generated at the period of 2 seconds, and in a case in which a message reception event occurs, vibration of one second may be generated at a period of 5 seconds.

Referring back to FIG. 23, when a multi-touch is received through the display unit 151 while the notification function regarding the generated event is being performed, the controller 180 may perform a predetermined response function regarding the generated event (S230). As discussed above, in a case in which an area of the multi-touch is larger than the predetermined area, the controller 180 may perform a specific response function corresponding to the generated event regardless of a touch reception position or the number of received touches.

FIGS. 24 through 27 are views illustrating examples of performing the method of driving an electronic device illustrated in FIG. 23.

(a) of FIG. 24 illustrates that a call reception event occurs in the mobile terminal 300 which interworks with the electronic device 100 and a multi-touch is received through the display unit 151, while the mobile terminal 300 performs a notification function regarding the call reception event.

When a multi-touch is received during the event occurrence notification operation, the controller 180 of the electronic device 100 may interrupt a notification function using an audio signal and a notification function through vibration, among call reception notification functions of the mobile terminal 300, as illustrated in (b) of FIG. 24.

The controller 180 may perform a call connection function on the basis of the multi-touch reception. Here, communication according to the call connection may be performed through the electronic device 100 or an earphone 400 interworking with the mobile terminal 300. Although not shown, the earphone 400 includes a microphone.

Unlike the case illustrated in FIG. 24, the controller 180 may perform a call function using the audio output unit 152 and the microphone 122 installed in the electronic device 100. Also, the controller 180 may display only image data indicating that a call connection is being performed, on the display unit 151, and may cause an actual call function to be performed in the mobile terminal 300.

Meanwhile, the aforementioned operation may also be performed even when a multi-touch is received in a state in which a graphic user interface (GUI) for notification of occurrence of a call reception event is not provided as illustrated in (a) of FIG. 24. This is the same in the examples of FIGS. 25 through 27 (to be described hereinafter). Here, preferably, an area of the multi-touch is a predetermined area or larger. This is to allow a response function regarding the generated event to be performed intuitionally and easily through only the simple multi-touch having the predetermined area or larger even during exercise.

Referring to FIG. 25, in a case in which a multi-touch is received while a function of notifying about a call reception event that occurs in the mobile terminal 300 is being performed, the controller 180 may provide a GUI for selecting a response form with respect to the call reception event through the display unit 151. Then, the user may perform a touch through the GUI to connect a call or perform a rejection function. Meanwhile, in a case in which a touch through the GUI is not received within a predetermined time after the multi-touch is received, the controller 180 may release providing of the GUI.

(a) of FIG. 26 illustrates that a multi-touch is received through the display unit 151 while a notification function is being performed as a message reception event occurs in the mobile terminal 300.

Then, as illustrated in (b) of FIG. 26, the controller 180 may convert a received message into a voice message and output the voice message through the earphone 400. Here, the conversion of the received message may be performed in the electronic device 100 or in the mobile terminal 300. According to circumstances, outputting of the converted voice may be performed by the audio output unit 152 installed in the electronic device 100 or may be performed through an audio output unit of the mobile terminal 300.

Figure 27:
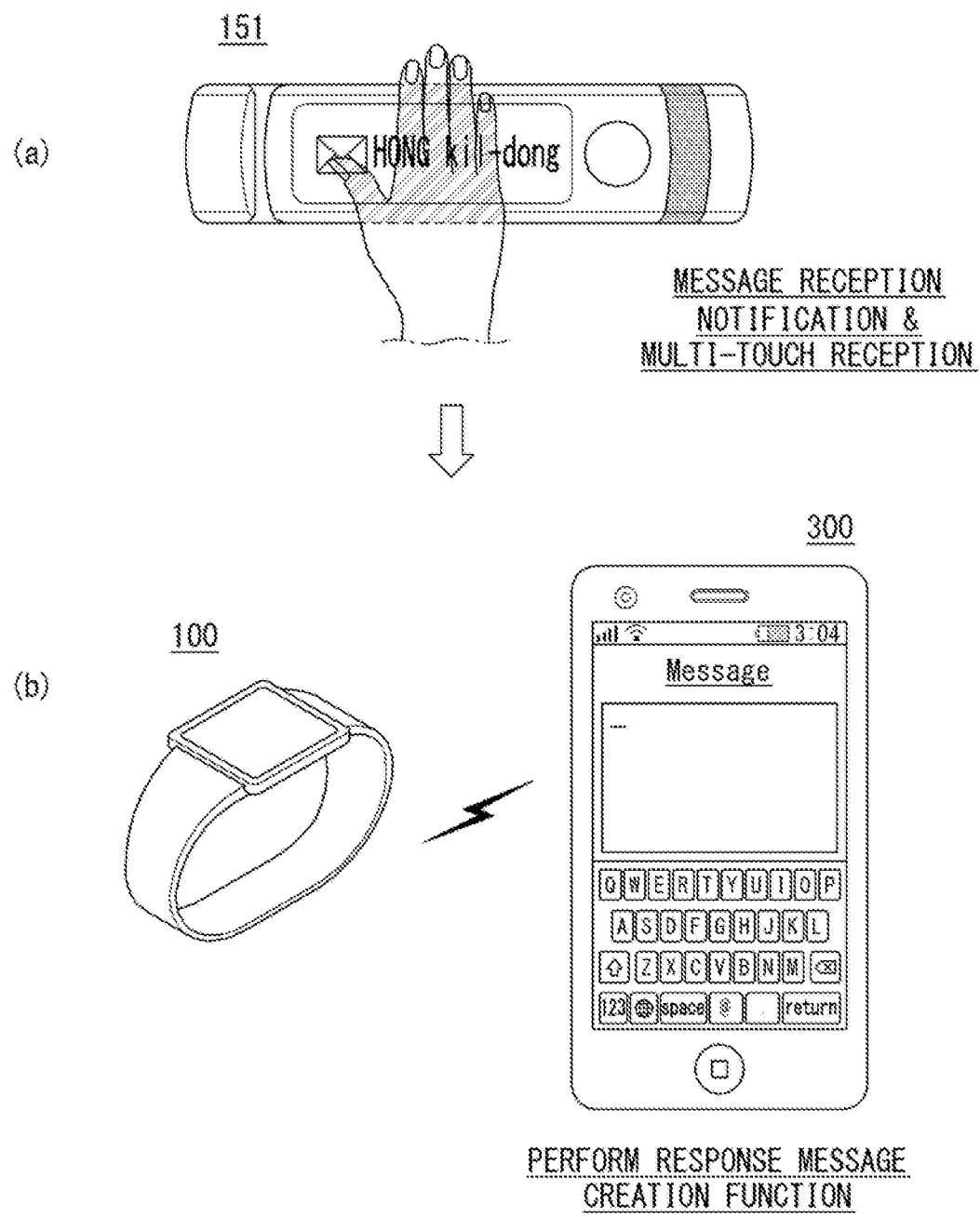

Referring to FIG. 27, THE electronic device 100 may control the mobile terminal 300 to perform a response message creation function with respect to the received message on the basis of a multi-touch received while the message reception event notification function is being performed.

Figure 28:
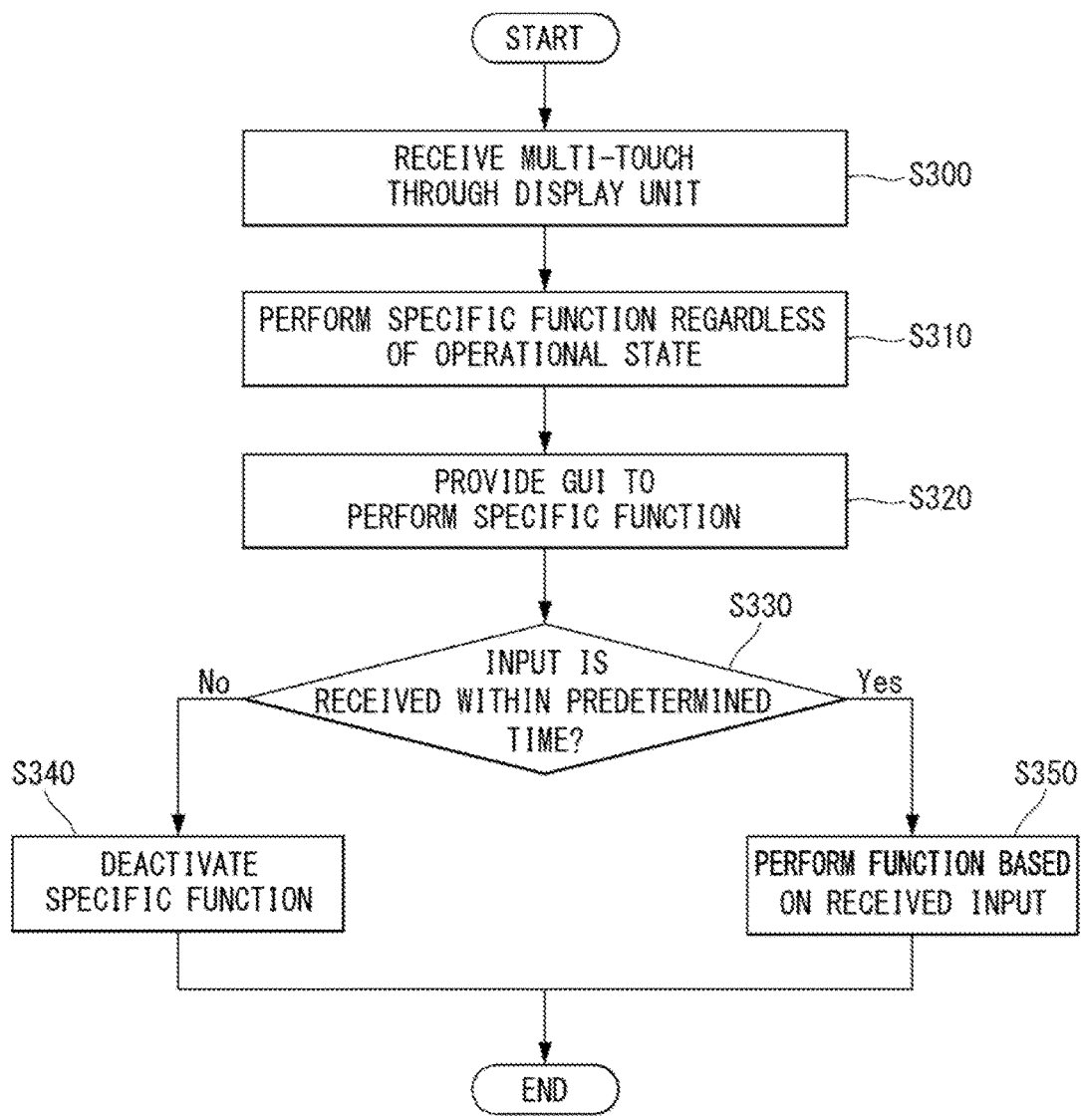
FIG. 28 is a flow chart illustrating another example of a method for driving an electronic device according to an embodiment of the present disclosure.

FIG. 28 is a flow chart illustrating another example of a method of driving an electronic device according to an embodiment of the present disclosure. The driving method will be described with reference to relevant drawings.

A multi-touch is received through the display unit (S300). Then, the controller 180 of the electronic device 100 may perform a specific function regardless of operational state of the electronic device 100 (S310) and provide a GUI for performing the specific function to the display unit 151 (S320).

For example, when an area of the multi-touch is larger than a predetermined area, the controller 180 may disregard the GUI provided through the display unit 151 and perform a predetermined specific function.

After the GUI is provided through the display unit 151, the controller 180 may determine whether a predetermined input is received through the GUI within a predetermined time (S330). When a touch through the GUI is not received within the predetermined time, the controller 180 may deactivate the specific function and release providing of the GUI.

Meanwhile, the controller 180 may further consider an input through other input unit, in addition to a touch through the GUI. For example, even though a touch through the GUI is not received within the predetermined time, when manipulation through an input button, or the like, is recognized, the controller 180 may not deactivate the specific function.

However, when an input (i.e., a touch) is received within the predetermined time through the GUI, the controller 180 may perform a specific function on the basis of the received input (S350).

Figure 29:
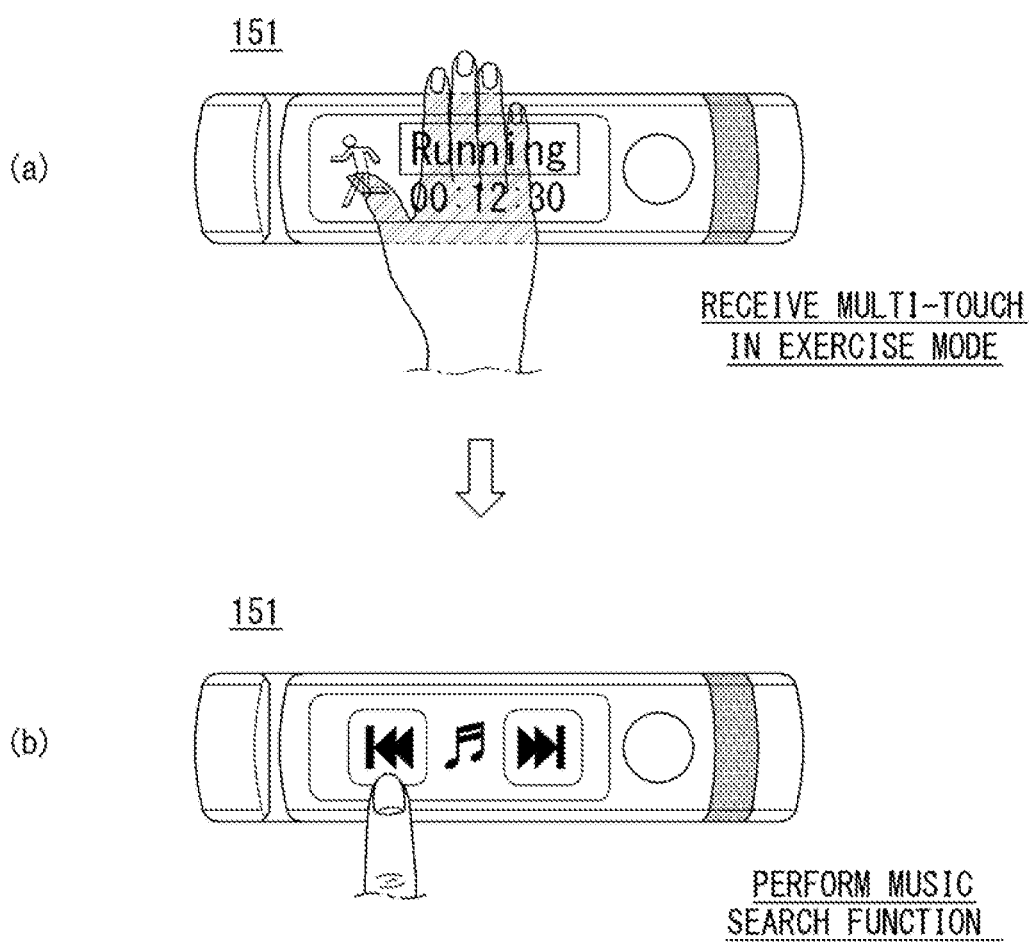
FIG. 29 is a view illustrating an example of performing the method of driving an electronic device illustrated in FIG. 28.

FIG. 29 is a view illustrating an example of performing the method of driving an electronic device illustrated in FIG. 28.

(a) of FIG. 29 illustrates that a multi-touch having a predetermined area or larger is received through the display unit 151. Then, as illustrated in (b) of FIG. 29, the controller 180 of the electronic device 100 may disregard an operational state of the electronic device 100 or a touch with respect to the GUI displayed on the display unit 151 and perform a music search function previously determined to correspond to the multi-touch.

Then, the user may perform a music search function through a music search GUI provided through the display unit 151. Meanwhile, in a case in which a touch is not received through the GUI provided through the display unit 151 during a predetermined time, the controller 180 may deactivate the music search function and release providing of the GUI.

Meanwhile, unlike the case of FIG. 29, the controller 180 may not display the GUI supporting the music search function on the display unit 151. Here, the user may perform the music search function using a different input unit provided in the electronic device 100.

In addition, when the music search function is activated on the basis of the multi-touch, the controller 180 may recognize a touch received through the display unit 151 as a music search dedicated touch. For example, when a touch in a horizontal direction is received, the controller 180 may perform the music search function, disregarding the GUI displayed on the display unit 151, during a predetermined period of time after the multi-touch is received.

FIG. 30 is a view illustrating an example of a music search function provided in the electronic device 100 according to an embodiment of the present disclosure.

(a) of FIG. 30 illustrates that a Z-shaped touch, as a touch previously matched to the music search function, is received in a state in which music is being played in an exercise mode and a GUI corresponding to the exercise mode is displayed on the display unit 151.

Then, as illustrated in (b) of FIG. 30, the controller 180 of the electronic device 100 may activate the music search function through a flicking touch in a horizontal direction.

Meanwhile, when the flicking touch is not received within a predetermined period of time after the Z-shaped touch is received, the controller 180 may deactivate the music search function.

Unlike the example of FIG. 30, in a case in which a predetermined type of touch is received through the display unit 151, the controller 180 may provide a GUI for performing a function previously determined to correspond to the predetermined type of touch through the display unit 151. Also, in this case, if a touch through the GUI is not received during a predetermined period of time, the controller 180 may release providing of the GUI.

Meanwhile, the predetermined type of touch matched to the specific function in the electronic device 100 is not limited to the Z-shaped touch, and the specific function corresponding to the predetermined type of touch is not limited to the music search function.

Figure 31:
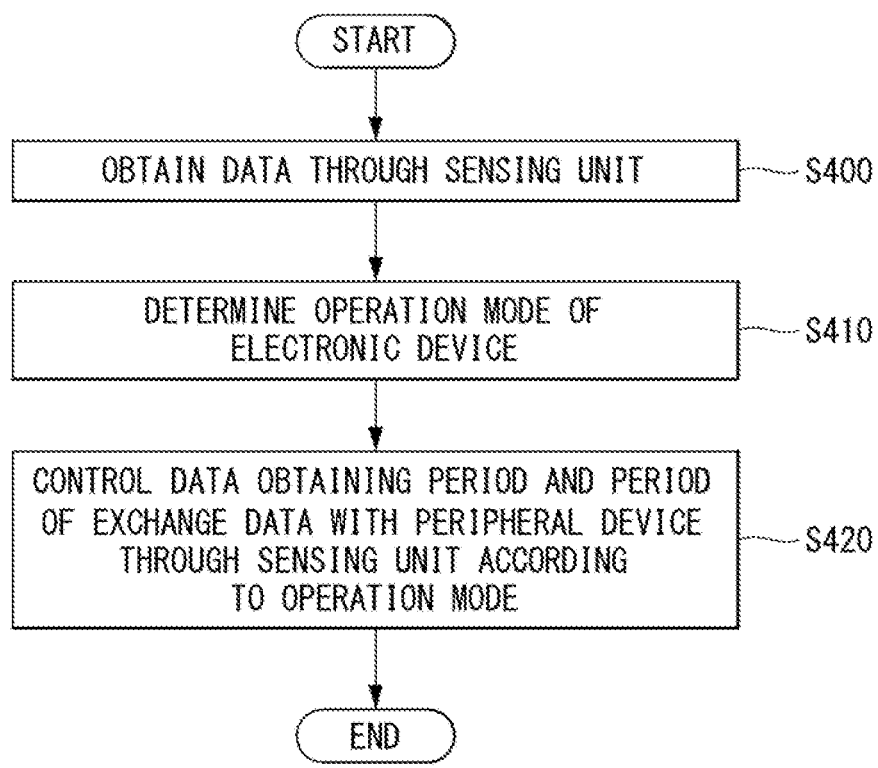
FIG. 31 is a flow chart illustrating another example of a method for driving an electronic device according to an embodiment of the present disclosure.

FIG. 31 is a flow chart illustrating another example of a method for driving an electronic device according to an embodiment of the present disclosure. Hereinafter, the driving method will be described with reference to the relevant drawings.

The controller 180 of the electronic device 100 controls the sensing unit 140 to obtain data (S400). Thereafter, the controller 180 may determine an operation mode of the electronic device 100 on the basis of data obtained through the sensing unit 140 (S410). Here, the data obtained through the sensing unit 140 may include data regarding movement of the user and a surrounding environment.

The operation mode of the electronic device 100 may include an exercise mode, a normal mode, a sleep mode, and the like. As described above, the normal mode refers to a mode in which exercise data of the user is created on the basis of data obtained through the sensing unit 140. The electronic device 100 may perform a function such as a music play function or a video play function even in the exercise mode.

The normal mode may refer to a case in which the electronic device 100 does not operate as a general multimedia device in a state in which a function of creating exercise data of the user is not performed. For example, a state in which a predetermined application is performed in a state in which the function of creating exercise data of the user is not performed in the electronic device 100 may be included in the normal mode.

The sleep mode may refer to a case in which the electronic device 100 does not perform any function for a predetermined period of time or longer. In the sleep mode, a majority of components excluding primary components of the electronic device 100, may be deactivated.

Referring back to FIG. 31, the controller 180 may control a data obtaining period through the sensing unit 140 and a period of exchanging data with an interworking peripheral device according to a determined operation mode (S420). For example, the controller 180 may control the data sensing period in the exercise mode and the period of exchanging data with a peripheral device to be shorter than that in the normal mode.

The embodiments of the present invention have been described in detail, but the scope of the present invention is not limited thereto and various variants and modifications by a person skilled in the art using a basic concept of the present invention defined in claims also belong to the scope of the present invention.

INDUSTRIAL APPLICABILITY

The electronic device according to an embodiment of the present disclosure may manage exercise-related data of a user who wears the electronic device and may interwork with a peripheral device through short-range wireless communication to perform various functions, and thus, the electronic device may be used in various industrial fields such as a multimedia device field, a healthcare-related field, and a training-related field.

The exemplary embodiments of the present disclosure will now be described with reference to the accompanying drawings, in which like numbers refer to like elements throughout. In describing the present disclosure, if a detailed explanation for a related known function or construction is considered to unnecessarily divert the gist of the present disclosure, such explanation has been omitted but would be understood by those skilled in the art. The accompanying drawings of the present disclosure aim to facilitate understanding of the present disclosure and should not be construed as limited to the accompanying drawings. The technical idea of the present disclosure should be interpreted to embrace all such alterations, modifications, and variations in addition to the accompanying drawings.

The invention claimed is:

1. An electronic device having a band to be worn on a human body, the electronic device comprising:
    a display unit configured to support a touch screen function;
    a wireless communication unit configured to support a short-range wireless communication function to interwork with a peripheral device;
    a sensing unit configured to sense movement of a body of a user who wears the electronic device; and
    a controller connected to the display unit, the wireless communication unit and the sensing unit, and configured to:
    control the display unit to display a user interface corresponding to an operational state of the electronic device, the user interface including at least one item and each of the at least one item corresponding to at least one function,
    receive, via the display unit, a touch input,
    determine whether the touch input is a multi-touch, the multi-touch being a touch on the display unit with a palm or a plurality of fingers,
    perform an item corresponding to a position of the touch input on the at least one item when the touch input is not the multi-touch, and
    generate a control signal corresponding to, regardless of a position of the touch input, when the touch input is the multi-touch, the control signal being different from that of a touch using a finger applied to a specific spot,
    control to perform a specific function using the control signal,
    perform the specific function regardless of an operational state of the electronic device and provide a GUI for performing the specific function to the display unit, and
    control a data obtaining period through the sensing unit and a period of exchanging data with an interworking peripheral device according to a determined operation mode,
    wherein the determined operation mode is determined from among an exercise mode and a normal mode, and
    wherein the controller is further configured to control the data obtaining period in the exercise mode and the period of exchanging data with the interworking peripheral device to be shorter than that in the normal mode.

2. The electronic device of claim 1, further comprising:
a haptic module configured to perform a function of providing information through tactile sensation,
wherein the controller is configured control the display unit and the haptic module to perform a notification function regarding an event which has occurred in the peripheral device, and
when the multi-touch is received while the notification function regarding the generated event is being performed, the controller is configured control the peripheral device to perform a predetermined response function regarding the generated event.

3. The electronic device of claim 2, wherein the controller is configured control the haptic module to generate vibrations having different patterns according to the event which has occurred in the peripheral device.

4. The electronic device of claim 2, wherein when a call reception event occurs in the peripheral device and the multi-touch is received while a notification function regarding the call reception event is being performed, the controller is configured control the peripheral device to interrupt a call reception notification function using a sound or vibration in the peripheral device.

5. The electronic device of claim 4, wherein when the multi-touch is received while the notification function regarding the call reception event is being performed, the controller is configured provide a user interface for determining a response form corresponding to the call reception event through the display unit.

6. The electronic device of claim 2, wherein when a message reception event occurs in the peripheral device and the multi-touch is received while a notification function regarding the message reception event is being performed, the controller is configured control the peripheral device to convert a received message into a voice and output the converted voice.

7. The electronic device of claim 1, wherein the controller is configured determine an operation mode of the electronic device on the basis of data obtained through the sensing unit.

8. The electronic device of claim 1, wherein when a predetermined type of touch is received through the display unit, the controller is configured execute a specific function corresponding to the received touch regardless of the operational state of the electronic device.

9. The electronic device of claim 8, wherein when an additional touch is not received through the display unit within a predetermined time after the specific function is executed on the basis of the received touch, the controller is configured terminate execution of the specific function.

10. The electronic device of claim 8, wherein the controller provides a user interface corresponding to the specific function to the display unit, and when a touch through the user interface is not received within a predetermined time after the user interface is performed, the controller is configured release displaying of the user interface.

* * * * *